(12) United States Patent
Gabazza et al.

(10) Patent No.: US 9,637,743 B2
(45) Date of Patent: *May 2, 2017

(54) PREVENTIVE OR THERAPEUTIC AGENT FOR FIBROSIS

(71) Applicants: Mie University, Tsu-shi (JP); Otsuka Pharmaceutical Co., Ltd., Tokyo (JP)

(72) Inventors: Esteban C Gabazza, Tsu (JP); Tetsu Kobayashi, Tsu (JP); Hidekazu Toyobuku, Osaka (JP); Ayako Fukuda, Osaka (JP); Tetsuya Hasegawa, Osaka (JP)

(73) Assignees: MIE UNIVERSITY, Tsu-shi (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,204

(22) Filed: Jan. 19, 2016

(65) Prior Publication Data

US 2016/0130586 A1 May 12, 2016

Related U.S. Application Data

(63) Continuation of application No. 14/272,898, filed on May 8, 2014, now Pat. No. 9,273,314, which is a continuation of application No. 13/824,080, filed as application No. PCT/JP2011/073628 on Oct. 14, 2011, now Pat. No. 8,772,262.

(30) Foreign Application Priority Data

Oct. 14, 2010 (JP) ................................. 2010-231946

(51) Int. Cl.
  *C12N 15/113* (2010.01)
  *A61K 31/713* (2006.01)
  *C07H 21/02* (2006.01)

(52) U.S. Cl.
  CPC ........ *C12N 15/1136* (2013.01); *A61K 31/713* (2013.01); *C07H 21/02* (2013.01); *C12N 15/113* (2013.01); *C12N 2310/14* (2013.01); *C12N 2310/315* (2013.01); *C12N 2320/30* (2013.01)

(58) Field of Classification Search
  None
  See application file for complete search history.

(56) References Cited

U.S. PATENT DOCUMENTS

| | | |
|---|---|---|
| 2004/0001811 A1 | 1/2004 | Kreutzer et al. |
| 2004/0038921 A1 | 2/2004 | Kreutzer et al. |
| 2004/0053875 A1 | 3/2004 | Kreutzer et al. |
| 2004/0072779 A1 | 4/2004 | Kreutzer et al. |
| 2004/0091457 A1 | 5/2004 | Kreutzer et al. |
| 2004/0102408 A1 | 5/2004 | Kreutzer et al. |
| 2004/0121348 A1 | 6/2004 | Kreutzer et al. |
| 2004/0126791 A1 | 7/2004 | Wajant et al. |
| 2004/0175703 A1 | 9/2004 | Kreutzer et al. |
| 2004/0248835 A1 | 12/2004 | Krebs et al. |
| 2005/0074757 A1 | 4/2005 | Kreutzer et al. |
| 2005/0100907 A1 | 5/2005 | Kreutzer et al. |
| 2005/0119202 A1 | 6/2005 | Kreutzer et al. |
| 2005/0176667 A1 | 8/2005 | Vornlocher |
| 2006/0084621 A1 | 4/2006 | Vornlocher |
| 2007/0269815 A1 | 11/2007 | Rivory et al. |
| 2008/0015161 A1 | 1/2008 | Vornlocher et al. |
| 2008/0070856 A1 | 3/2008 | Kreutzer et al. |
| 2008/0166800 A1 | 7/2008 | Kreutzer et al. |
| 2008/0171861 A1 | 7/2008 | Kreutzer et al. |
| 2008/0171862 A1 | 7/2008 | Kreutzer et al. |
| 2008/0182981 A1 | 7/2008 | Kreutzer et al. |
| 2008/0194512 A1 | 8/2008 | John et al. |
| 2008/0233651 A1 | 9/2008 | Kreutzer et al. |
| 2008/0242851 A1 | 10/2008 | Khvorova et al. |
| 2008/0261303 A1 | 10/2008 | Kreutzer et al. |
| 2008/0286866 A1 | 11/2008 | Quay et al. |
| 2008/0287383 A1 | 11/2008 | Quay et al. |
| 2008/0293136 A1 | 11/2008 | Quay et al. |
| 2008/0299659 A1 | 12/2008 | Quay et al. |
| 2008/0317839 A1 | 12/2008 | Quay et al. |
| 2009/0053808 A1 | 2/2009 | Vornlocher |
| 2009/0192103 A1 | 7/2009 | Rivory et al. |
| 2009/0239816 A1 | 9/2009 | Rivory et al. |
| 2010/0015706 A1 | 1/2010 | Quay et al. |
| 2010/0041140 A1 | 2/2010 | Quay et al. |
| 2010/0047909 A1 | 2/2010 | Quay et al. |
| 2010/0055782 A1 | 3/2010 | Quay et al. |
| 2010/0055783 A1 | 3/2010 | Quay et al. |
| 2010/0055784 A1 | 3/2010 | Quay et al. |

(Continued)

FOREIGN PATENT DOCUMENTS

| | | |
|---|---|---|
| JP | 2007 119396 | 5/2007 |
| JP | 2009 516517 | 4/2009 |

(Continued)

OTHER PUBLICATIONS

Moore, L., et al., "Silencing of Transforming Growth Factor-β1 In situ by RNA Interference for Breast Cancer: Implications for Proliferation and Migration In vitro and Metastasis in vivo," Clin. Cancer Res., vol. 14, No. 15, pp. 4961-4970, (Aug. 1, 2008).

Yu, W., et al., "Inhibitive effect of specific stealth siRNAs on TGF-β1 expression of mouse lung fibroblasts," Di-San Junyi Daxue Xuebao Bianjibu, vol. 29, No. 21, pp. 2038-2040, (Nov. 2007) (with English abstract).

International Search Report Issued Nov. 29, 2011 in PCT/JP11/73628 Filed Oct. 14, 2011.

Lai, T.C., et al., "Small Interfering RNAs (siRNAs) Targeting TGF-β1 mRNA Suppress Asbestos-Induced Expression of TGF-β1 and CTGF in Fibroblasts," J. Environ. Pathol. Toxicol. Oncol., vol. 28, No. 2, pp. 109-119, (2009).

(Continued)

*Primary Examiner* — Tracy Vivlemore
(74) *Attorney, Agent, or Firm* — Oblon, McClelland, Maier & Neustadt, L.L.P.

(57) ABSTRACT

Provided is siRNA effective for the treatment of fibrosis and a pharmaceutical containing the siRNA.

23 Claims, 3 Drawing Sheets

(56) References Cited

U.S. PATENT DOCUMENTS

| | | |
|---|---|---|
| 2010/0105134 A1 | 4/2010 | Quay et al. |
| 2010/0112687 A1 | 5/2010 | Quay et al. |
| 2010/0291194 A1 | 11/2010 | Kreutzer et al. |
| 2010/0316699 A1 | 12/2010 | John et al. |
| 2010/0319074 A1 | 12/2010 | Lu et al. |
| 2011/0105590 A1 | 5/2011 | Vornlocher |
| 2011/0111493 A1 | 5/2011 | Kreutzer et al. |
| 2011/0287090 A1 | 11/2011 | Kreutzer et al. |
| 2012/0108646 A1 | 5/2012 | Vornlocher et al. |
| 2012/0115923 A1 | 5/2012 | He et al. |

FOREIGN PATENT DOCUMENTS

| | | |
|---|---|---|
| JP | 2010 172344 | 8/2010 |
| JP | 2010 528985 | 8/2010 |
| WO | 03 035083 | 5/2003 |
| WO | 2007 079224 | 7/2007 |
| WO | 2007 109097 | 9/2007 |
| WO | 2008 109548 | 9/2008 |
| WO | 2009 061417 | 5/2009 |
| WO | 2011119887 | 9/2011 |

OTHER PUBLICATIONS

Ui-Tei, K., et al., "Functional dissection of siRNA sequence by systematic DNA substitution: modified siRNA with a DNA seed arm is a powerful tool for mammalian gene silencing with significantly reduced off-target effect," Nucleic Acids Research, vol. 36, No. 7, pp. 2136-2151, (2008).

Wang, Z., et al., "Inhibition of Smad3 expression decreases collagen synthesis in keloid disease fibroblasts," Journal of Plastic, Reconstructive & Aesthetic Surgery, vol. 60, pp. 1193-1199, (2007).

Hwang, M., et al., "TGF-$\beta$1 si RNA suppresses the tubulointerstitial fibrosis in the kidney of ureteral obstruction," Experimental and Molecular Pathology, vol. 81, pp. 48-54, (2006).

Takabatake, Y., et al., "Exploring RNA interference as a therapeutic strategy for renal disease," Gene Therapy, vol. 12, pp. 965-973, (Feb. 24, 2005).

Xu, W., et al., "Effects of RNA interference targeting transforming growth factor-beta 1 on immune hepatic fibrosis induced by Concanavalin A in mice," Hepatobiliary Pancreat Dis Int, vol. 8, No. 3, Total 9 Pages, (Jun. 15, 2009).

Liu, X.J., et al., "Antagonism of transforming growth factor-$\beta$ signaling inhibits fibrosis-related genes," Biotechnology Letters, vol. 27, pp. 1609-1615, (Aug. 15, 2005).

"Inhibition of TGF-B-Induced Activation of Lung Fibroblasts by Smad-Specific siRNA," The Journal of the Japanese Respiratory Society, vol. 46, Total 4 Pages, (May 2008) (with partial English translation).

US 9,637,743 B2

PREVENTIVE OR THERAPEUTIC AGENT FOR FIBROSIS

This application is a continuation application of U.S. Ser. No. 14/272,898 filed May 8, 2014, allowed, which is a continuation of U.S. Ser. No. 13/824,080 filed Mar. 15, 2013, U.S. Pat. No. 8,772,262, incorporated herein by reference, which was a National Stage of PCT/JP11/073628 filed Oct. 14, 2011 and claims the benefit of JP 2010-231946 filed Oct. 14, 2010.

TECHNICAL FIELD

The present invention relates to a therapeutic agent for fibrosis. Specifically, the present invention relates to small interfering RNA (siRNA) targeting a gene encoding transforming growth factor (TGF)-β1 and a pharmaceutical containing the siRNA.

BACKGROUND ART

Pulmonary fibrosis refers to a symptom in which lung tissues become fibrotic due to the accumulation of excess collagen and other extracellular matrix. Within a classification of pulmonary fibrosis, idiopathic pulmonary fibrosis is a chronic intractable disease, carrying a poor prognosis with an average median survival time of three years and a five year survival rate of 20 to 40%. For the treatment of pulmonary fibrosis, steroid drugs and immunosuppressants are used; however, no effective therapy which can improve the prognosis is currently available, and thus development of a new therapeutic drug is demanded.

Recently, it has been revealed that there are many diseases whose onset is attributed to a gene, and many genes are also reported to be involved in pulmonary fibrosis (Patent Documents 1 to 4, Non Patent Documents 1 to 6). As the main factor associated with pulmonary fibrosis, TGF-β1 (Patent Documents 1 and 2, Non Patent Documents 2 to 6), Smad3 (Non Patent Document 1), MCP-1 (Patent Document 3), and the like are reported.

Meanwhile, a nucleic acid, particularly, siRNA induces degradation of mRNA of a gene having a sequence identical or almost identical to a specific sequence present in a cell, thereby inhibiting the expression of a target gene (RNA interference). Accordingly, the function of inhibiting the expression of the target gene because of RNA interference is useful for the amelioration or treatment of disease symptoms induced by abnormal expression of a specific gene or a group of genes. As to the pulmonary fibrosis-associated genes as well, there are reports that inhibition of the expression of those genes with siRNA was attempted (Patent Documents 1 to 4, Non Patent Documents 1 to 6).

However, the technologies reported to date have only exhibited inhibitory effect of an siRNA sequence on a disease-associated gene in experimental animals (mice and rats), while they have not sufficiently exhibited effects specifically on human genes. Further, concerning the inhibitory effect of siRNA, while the effects of siRNA at concentrations of 200 nM (Non Patent Document 1) and 20 to 500 nM (Non Patent Document 5) are exhibited, a nucleic acid molecule capable of inhibiting the expression of a pulmonary fibrosis-associated gene efficiently at a low concentration is not demonstrated.

Several tens of siRNAs targeting the TGF-β1 gene have been reported so far (Patent Documents 1 and 5 to 7). However, considering that the full-length TGF-β1 gene consists of 2346 bases (GenBank Accession No. NM_000660.3) and there are countless possible combinations of selecting an approximately 20-mer sequence out of the full-length gene, it is not easy to design an dsRNA or siRNA molecule capable of more efficiently inhibiting the expression of the gene from the combinations.

RELATED ART DOCUMENTS

Patent Documents

[Patent Document 1] WO2007/109097
[Patent Document 2] WO2003/035083
[Patent Document 3] JP-A-2007-119396
[Patent Document 4] JP-A-2009-516517
[Patent Document 5] WO2009/061417
[Patent Document 6] WO2008/109548
[Patent Document 7] WO2007/79224

Non Patent Documents

[Non Patent Document 1] Wang Z, Gao Z, Shi Y, Sun Y, Lin Z, Jiang H, Hou T, Wang Q, Yuan X, Zhu X, Wu H, Jin Y, J Plast Reconstr Aesthet Surg, 1193-1199, 60, 2007
[Non Patent Document 2] Hwang M, Kim H J, Noh H J, Chang Y C, Chae Y M, Kim K H, Jeon J P, Lee T S, Oh H K, Lee Y S, Park K K, Exp Mol Pathol, 48-54, 81, 2006
[Non Patent Document 3] Takabatake Y, Isaka Y, Mizui M, Kawachi H, Shimizu F, Ito T, Hori M, Imai E, Gene Ther, 965-973, 12, 2005
[Non Patent Document 4] Xu W, Wang L W, Shi J Z, Gong Z J, Hepatobiliary Pancreat Dis Int, 300-308, 8, 2009
[Non Patent Document 5] Liu X J, Ruan C M, Gong X F, Li. X Z, Wang H L, Wang M W, Yin J Q, Biotechnol Lett, 1609-1615, 27, 2005
[Non Patent Document 6] Jutaro Fukumoto, Saiko Suetsugu, Chika Harada, Tomonobu Kawaguchi, Naoki Hamada, Takashige Maeyama, Kazuyoshi Kuwano, and Yoichi Nakanishi, The Journal of The Japanese Respiratory Society, 185, 46, 2008

SUMMARY OF THE INVENTION

Problem to be Solved by the Invention

The present invention relates to provision of siRNA effective for the treatment of fibrosis and a pharmaceutical containing the siRNA.

Means for Solving the Problem

The present inventors have conducted intensive research to solve the aforementioned problem. As a result, they have found that specific siRNA targeting the human TGF-β1 gene can effectively inhibit the TGF-β1 expression in human cells, and further, improve the symptoms of pulmonary fibrosis in the lungs of a mouse model of pulmonary fibrosis without inducing the interferon reaction.

That is, the present invention relates to the following 1) to 19).

1) An siRNA having a full length of 30 or fewer nucleotides and targeting a sequence comprising 17 to 23 consecutive bases selected from the group consisting of bases at positions 1285 to 1318, bases at positions 1398 to 1418, bases at positions 1434 to 1463, bases at positions 1548 to 1579, bases at positions 1608 to 1628, bases at positions 1700 to 1726, bases at positions 1778 to 1798, bases at positions 1806 to 1826, and bases at positions 1887 to 1907 of SEQ ID NO: 1.

2) The siRNA according to the aforementioned 1), which is selected from the following (a) to (s):

(a) an siRNA comprising a sense sequence of SEQ ID NO: 2 and an antisense sequence of SEQ ID NO: 3;

(b) an siRNA comprising a sense sequence of SEQ ID NO: 4 and an antisense sequence of SEQ ID NO: 5;

(c) an siRNA comprising a sense sequence of SEQ ID NO: 6 and an antisense sequence of SEQ ID NO: 7;

(d) an siRNA comprising a sense sequence of SEQ ID NO: 8 and an antisense sequence of SEQ ID NO: 9;

(e) an siRNA comprising a sense sequence of SEQ ID NO: 10 and an antisense sequence of SEQ ID NO: 11;

(f) an siRNA comprising a sense sequence of SEQ ID NO: 12 and an antisense sequence of SEQ ID NO: 13;

(g) an siRNA comprising a sense sequence of SEQ ID NO: 14 and an antisense sequence of SEQ ID NO: 15;

(h) an siRNA comprising a sense sequence of SEQ ID NO: 16 and an antisense sequence of SEQ ID NO: 17;

(i) an siRNA comprising a sense sequence of SEQ ID NO: 18 and an antisense sequence of SEQ ID NO: 19;

(j) an siRNA comprising a sense sequence of SEQ ID NO: 20 and an antisense sequence of SEQ ID NO: 21;

(k) an siRNA comprising a sense sequence of SEQ ID NO: 22 and an antisense sequence of SEQ ID NO: 23;

(l) an siRNA comprising a sense sequence of SEQ ID NO: 24 and an antisense sequence of SEQ ID NO: 25;

(m) an siRNA comprising a sense sequence of SEQ ID NO: 26 and an antisense sequence of SEQ ID NO: 27;

(n) an siRNA comprising a sense sequence of SEQ ID NO: 28 and an antisense sequence of SEQ ID NO: 29;

(o) an siRNA comprising a sense sequence of SEQ ID NO: 30 and an antisense sequence of SEQ ID NO: 31;

(p) an siRNA comprising a sense sequence of SEQ ID NO: 32 and an antisense sequence of SEQ ID NO: 33;

(q) an siRNA comprising a sense sequence of SEQ ID NO: 34 and an antisense sequence of SEQ ID NO: 35;

(r) an siRNA comprising a sense sequence of SEQ ID NO: 36 and an antisense sequence of SEQ ID NO: 37; and (s) an siRNA comprising a sense sequence of SEQ ID NO: 54 and an antisense sequence of SEQ ID NO: 55.

3) The siRNA according to the aforementioned 1) or 2), wherein 1 to 10 consecutive nucleotides excluding an overhang nucleotide from the 3' terminus of the sense strand of the siRNA are converted into DNA.

4) The siRNA according to the aforementioned 1) to 3), wherein 1 to 10 consecutive nucleotides from the 5' terminus of the antisense strand of the siRNA are converted into DNA.

5) The siRNA according to the aforementioned 1) to 4), wherein 1 to 10 consecutive nucleotides excluding an overhang nucleotide from the 3' terminus of the sense strand of the siRNA are converted into DNA and 1 to 10 consecutive nucleotides from the 5' terminus of the antisense strand of the siRNA are converted into DNA.

6) The siRNA according to the aforementioned 1) to 5), wherein the 5' terminus of the antisense strand is monophosphorylated or monothiophosphorylated.

7) A pharmaceutical composition containing the siRNA according to any of the aforementioned 1) to 6).

8) A TGF-β1 gene expression inhibitor containing the siRNA according to any of the aforementioned 1) to 6) as an active ingredient.

9) A preventive or therapeutic agent for fibrosis containing the siRNA according to any of the aforementioned 1) to 6) as an active ingredient.

10) A preventive or therapeutic agent for pulmonary fibrosis or lung cancer containing the siRNA according to any of the aforementioned 1) to 6) as an active ingredient.

11) Use of the siRNA according to the aforementioned 1) to 6) for the production of a TGF-β1 gene expression inhibitor.

12) Use of the siRNA according to the aforementioned 1) to 6) for the production of a preventive or therapeutic agent for fibrosis.

13) Use of the siRNA according to the aforementioned 1) to 6) for the production of a preventive or therapeutic agent for pulmonary fibrosis or lung cancer.

14) The siRNA according to the aforementioned 1) to 6) for use in inhibiting TGF-β1 gene expression.

15) The siRNA according to the aforementioned 1) to 6) for use in preventing or treating fibrosis.

16) The siRNA according to the aforementioned 1) to 6) for use in preventing or treating pulmonary fibrosis or lung cancer.

17) A method for inhibiting TGF-β1 gene expression, comprising administering the siRNA according to the aforementioned 1) to 6) to a human or animal.

18) A method for preventing or treating fibrosis, comprising administering the siRNA according to the aforementioned 1) to 6) to a human or animal.

19) A method for preventing or treating pulmonary fibrosis or lung cancer, comprising administering the siRNA according to the aforementioned 1) to 6) to a human or animal.

Effects of the Invention

Since the siRNA of the present invention can efficiently suppress or inhibit the TGF-β1 expression at a low concentration, it is useful as a pharmaceutical for preventing or treating fibrosis.

MODE FOR CARRYING OUT THE INVENTION

Figure 1:
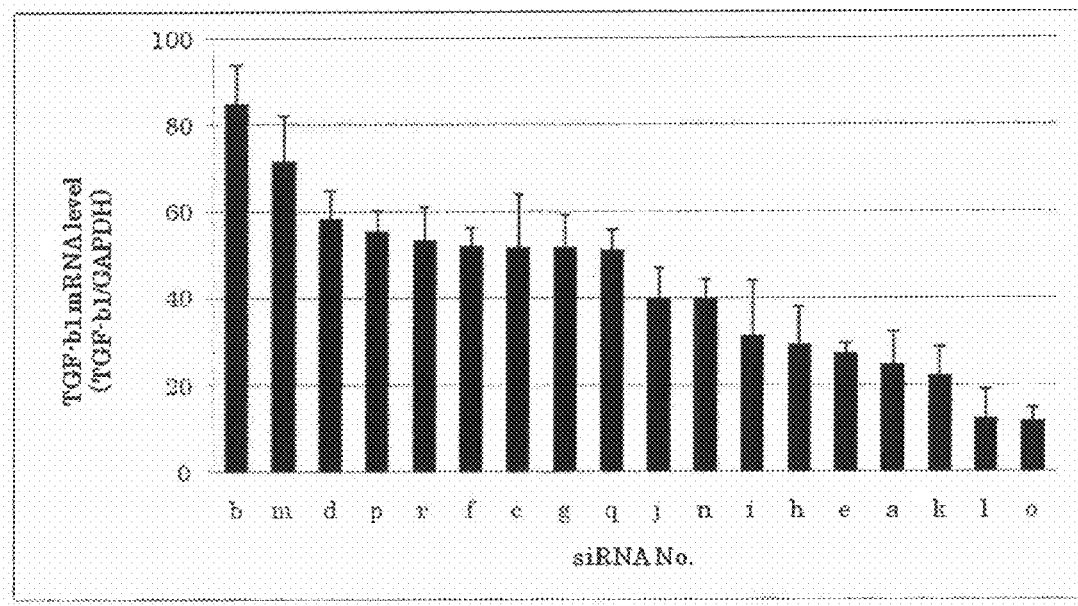
FIG. 1 is a graph showing the rate of inhibition of the expression of TGF-β1 mRNA by siRNA.

The sequence targeted by the siRNA of the present invention consists of 17 to 23 consecutive bases selected from the group consisting of bases at positions 1285 to 1318, bases at positions 1398 to 1418, bases at positions 1434 to 1463, bases at positions 1548 to 1579, bases at positions 1608 to 1628, bases at positions 1700 to 1726, bases at positions 1778 to 1798, bases at positions 1806 to 1826, and bases at positions 1887 to 1907 of SEQ ID NO: 1. Here, the 17 to 23 consecutive bases selected from each group are preferably 19 to 23 bases, and more preferably 21 bases.

The base sequence of SEQ ID NO: 1 represents the base sequence of TGF-β1 mRNA, and this sequence information is registered with GenBank under the GenBank Accession No. NM_000660.3.

The siRNA of the present invention is formed by hybridization of an antisense strand, which has a sequence complementary to the aforementioned target sequence of TGF-β1 mRNA, and a sense strand, which has a sequence complementary to this antisense strand. The siRNA of the present invention has a cleaving activity on TGF-β1 mRNA (i.e., RNA interference action) and an ability to inhibit the translation of this mRNA, namely, an ability to inhibit the expression of the TGF-β1 gene.

Regarding the nucleotide length of the siRNA of the present invention, the lengths of the sense strand and the antisense strand may be the same or different, and the full-length siRNA consists of 30 or fewer nucleotides, preferably 25 or fewer nucleotides, more preferably 23 or fewer nucleotides, or 21 nucleotides.

Further, both ends of the sense and antisense strands may be blunt ends or the 3' terminus of each strand may have an overhang (i.e., cohesive end). Here, the "blunt end" refers to a configuration in which, in the terminal region of double-stranded RNA, the terminal region of the sense strand and the corresponding terminal region of the antisense strand are paired up without forming a stretch of single strand. Further, the "overhang," also called a dangling end, refers to a configuration in which double-stranded RNA fails to form a double strand in the terminal region of the sense strand or the corresponding terminal region of the antisense strand due to the missing of a pairing base, generating a stretch of single strand (cohesive end).

As to the number of bases in the cohesive end portion, it consists of 1 to 10 nucleotides, preferably 1 to 4 nucleotides, and more preferably 1 to 2 nucleotides. It should be noted that there is no association in the length of the cohesive end between the two strands, and the two strands may each have a different length. The nucleotide in the cohesive end portion may be either RNA or DNA, and although it is preferably a base complementary to the target TGF-β1 mRNA, it may be a non-complementary base as long as the siRNA of the present invention retains the aforementioned RNA interference ability.

The siRNA of the present invention may be one double-stranded RNA composed of two separate strands. Besides that, it may also be a single strand RNA forming a double-stranded RNA through formation of a stem-loop structure. That is, the siRNA of the present invention also includes RNA forming a loop composed of 2 to 4 nucleotides at the 5' terminus of the sense strand and the 3' terminus of the antisense strand and RNA forming a loop composed of 2 to 4 nucleotides at the 3' terminus of the sense strand and the 5' terminus of the antisense strand. Further, it also includes RNA forming loops composed of 2 to 4 nucleotides at the 5' terminus of the sense strand and the 3' terminus of the antisense strand as well as the 3' terminus of the sense strand and the 5' terminus of the antisense strand.

The siRNA of the present invention and the target sequence are preferably identical; however, they may be substantially identical, i.e., have homologous sequences, as long as the siRNA can induce the aforementioned RNA interference. Specifically, as long as the sequence of the antisense strand of the siRNA of the present invention hybridizes with the target sequence, one or several (for example, two, three, and four) mismatches may be present. That is, the siRNA of the present invention includes siRNA having a sequence modified with the substitution, addition, or deletion of one or several bases relative to the target sequence and capable of inducing RNA interference, or siRNA having 85% or more, preferably 90% or more, preferably 95% or more, and more preferably 98% or more sequence identity to the target sequence and capable of inducing RNA interference.

It is to be noted that the hybridization conditions used herein refers to, when using the siRNA of the present invention as a pharmaceutical by administering it to the living body, the conditions in the living body, and when using the siRNA of the present invention as a reagent in vitro, moderately or highly stringent conditions. Examples of such conditions include hybridization conditions of 400 mM NaCl, 40 mM PIPES, pH 6.4, 1 mM EDTA, and a hybridization time of 12 to 160 hours at 50° C. to 70° C. These conditions are well known to those skilled in the art and described by Sambrook et al. (Molecular Cloning: A Laboratory Manual second edition, Cold Spring Harbor Laboratory Press, New York, USA, 1989).

Also, the sequence identity may be calculated by Lipman-Pearson method (Science, 227, 1435, (1985)), etc., and for example, it is calculated by using Search homology program of genetic information processing software Genetyx-Win (Ver.5.1.1; Software Development Co., Ltd.) with setting Unit size to compare (ktup) at 2.

Also, the siRNA of the present invention includes siRNA in which the nucleotides of either the sense strand or the antisense strand are entirely converted into DNA (hybrid siRNA) and siRNA in which the nucleotides of the sense and/or antisense strand are partially converted into DNA (chimeric siRNA), as long as the siRNA can induce the aforementioned RNA interference.

Herein, conversion of RNA nucleotide into DNA means conversion of AMP into dAMP, GMP into dGMP, CMP into dCMP, and UMP into dTMP.

As the hybrid siRNA, one in which the nucleotides of the sense strand are converted into DNA is preferable. Examples of the chimeric siRNA include one in which the nucleotides in the downstream side (i.e., the 3' terminal side of the sense strand and the 5' terminal side of the antisense strand) are partially converted into DNA. Specific examples thereof include one in which the nucleotides in the 3' terminal side of the sense strand and the 5' terminal side of the antisense strand are both converted into DNA and one in which the nucleotides of either the 3' terminal side of the sense strand or the 5' terminal side of the antisense strand are converted into DNA. Also, the length of the nucleotide to be converted is preferably any length up to be equivalent to ½ of the RNA molecule or shorter, for example, 1 to 13 nucleotides, preferably 1 to 10 nucleotides from the terminus. From the viewpoints of the RNA interference effect, and the stability, safety, etc. of the RNA molecule, examples of favorable chimeric siRNA include one in which the two strands each have a nucleotide length of 19 to 23, and 1 to 10, preferably 1 to 8, and more preferably 1 to 6 nucleotides excluding an overhang nucleotide(s) from the 3' terminus of the sense strand and 1 to 10, preferably 1 to 8, and more preferably 1 to 6 nucleotides from the 5' terminus of the antisense strand are consecutively converted into DNA in an arbitrary number (see [Table 2] to be shown below). Also, in this case, it is more preferable that the numbers of DNA converted in the sense strand (excluding a overhang nucleotide(s)) and the antisense strand be the same.

Also, the siRNA of the present invention may be one in which the nucleotide (i.e., ribonucleotide and deoxyribonucleotide) is a nucleotide analog having chemically modified sugar, base, and/or phosphate, as long as the siRNA can induce the aforementioned RNA interference. Examples of the nucleotide analog having a modified base include 5-position-modified uridine or cytidine (for example, 5-propynyluridine, 5-propynylcytidine, 5-methylcytidine, 5-methyluridine, 5-(2-amino)propyluridine, 5-halocytidine, 5-halouridine, and 5-methyloxyuridine); 8-position-modified adenosine or guanosine (for example, 8-bromoguanosine); deazanucleotide (for example, 7-deaza-adenosine); and O- and N-alkylated nucleotide (for example, N6-methyladenosine).

Also, examples of the nucleotide analog having a modified sugar include a 2'-position sugar modified analog, in which 2'-OH of the ribonucleotide is replaced by H, OR, R, a halogen atom, SH, SR, $NH_2$, NHR, $NR_2$, CN (wherein, R represents an alkyl, alkenyl, or alkynyl group having 1 to 6 carbon atoms), and the like, a 5'-terminal phosphorylated analog or a 5'-terminal monothiophosphorylated analog, in which the 5' terminal OH group is monophosphorylated or monothiophosphorylated.

Examples of the nucleotide analog having a modified phosphate include one in which a phosphoester group linking adjacent ribonucleotides is replaced by a phosphothioate group.

Also, aside from the aforementioned nucleotide analogs, the siRNA of the present invention may have a specific substituent or functional molecule bound to at least one of the first to sixth nucleotides from the 5' terminus or the 3' terminus of the sense strand (5' terminus, 3' terminus, or an internal base or sugar other than the terminus) directly or via a linker, and the substituent or functional molecule is preferably bound to at least one of the first to sixth, preferably the first to fourth nucleotides from the 5' terminus of the sense strand.

Here, examples of the substituent include an amino group; a mercapto group; a nitro group; an alkyl group having 1 to 40 (preferably 2 to 20, more preferably 4 to 12) carbon atoms; an aminoalkyl group having 1 to 40 (preferably 2 to 20, more preferably 4 to 12) carbon atoms; a thioalkyl group having 1 to 40 (preferably 2 to 20, more preferably 4 to 12) carbon atoms; an alkoxyl group having 1 to 40 (preferably 2 to 20, more preferably 4 to 12) carbon atoms; an aminoalkoxyl group having 1 to (preferably 2 to 20, more preferably 4 to 12) carbon atoms; a thioalkoxyl group having 1 to 40 (preferably 2 to 20, more preferably 4 to 12) carbon atoms; a mono- or di-alkyl amino group having 1 to 40 (preferably 2 to 20, more preferably 4 to 12) carbon atoms; an alkylthio group having 1 to 40 (preferably 2 to 20, more preferably 4 to 12) carbon atoms; a polyethylene oxide group having 2 to 40 (preferably 2 to 20, more preferably 4 to 12) carbon atoms; and a polypropylene oxide group having 3 to 39 (preferably 3 to 21, more preferably 3 to 12) carbon atoms. The RNA interference effect can be remarkably enhanced by binding these substituents.

Examples of the functional molecule include sugar, protein, peptide, amino acid, DNA, RNA (including tRNA), aptamers, modified nucleotides, low molecular weight organic and inorganic materials, cholesterol, dendrimers, lipid, and polymer materials. Through addition of these functional molecules, the siRNA of the present invention can attain excellent RNA interference effect and beneficial effect attributed to the functional molecules.

Examples of the aforementioned sugar include monosaccharides such as glucose, galactose, glucosamine, and galactosamine, and oligosaccharides or polysaccharides formed by an arbitrary combination of these monosaccharides.

As the aforementioned protein, proteins present inside the living body, proteins having pharmacological actions, proteins having molecular recognition actions, and the like can be used, and examples of these proteins include importin-β protein, avidin, and antibodies.

Specific examples of the aforementioned DNA include DNA of 5 to 50 bases in length, preferably 5 to 25 bases in length.

Examples of the aforementioned peptide include octa-arginine peptide R8, a nuclear localization signal peptide sequence (such as HIV-1 Tat and SV40T antigen), a nuclear export signal peptide (such as HIV-1 Rev and MAPKK), and a membrane fusion peptide. Examples of the aforementioned modified nucleotide include one having a modified phosphate skeleton such as phosphorothioate or boranophosphate DNA/RNA; a 2'-modified nucleotide such as 2'-OMe modified RNA and 2'-F modified RNA; a modified nucleotide in which the sugar molecules are cross-linked such as LNA (i.e., Locked Nucleic Acid) and ENA (i.e., 2'-O,4'-C-ethylene-bridged nucleic acids); and a modified nucleotide having a different basic skeleton such as PNA (i.e., peptide nucleic acid) and morpholino-nucleotide (see WO2008/140126 and WO2009/123185).

Examples of the aforementioned low molecular weight organic and inorganic materials include fluorescent materials such as Cy3 and Cy5; biotin; quantum dot; and fine gold particles. Examples of the aforementioned dendrimers include poly(amidoamine) dendrimer. Examples of the aforementioned lipid include, in addition to linoleic acid, 1,2-dioleoyl-sn-glycero-3-phosphoethanolamine (DOPE), etc., double-stranded lipid having two hydrophobic groups as described in WO2009/123185. Examples of the aforementioned polymer materials include polyethylene glycol and polyethylene imine.

Here, the group having a functional molecule may be the functional molecule residue per se, or a functional molecule residue to which one of the functional groups of a bifunctional linker is bound. That is, in the former case, the functional molecule is directly bound to a certain part of the aforementioned sense strand RNA, and in the latter case, the functional molecule is bound to a certain part of the aforementioned sense strand RNA via a bifunctional linker. Herein, no particular limitation is imposed on the bifunctional linker as long as it is a linker having two functional groups, and for example, N-succinimidyl 3-(2-pyridyldithio) propionate, N-4-maleimidobutyric acid, S-(2-pyridyldithio) cysteamine, iodoacetoxysuccinimide, N-(4-maleimidobutyryloxy)succinimide, N-[5-(3'-maleimidopropylamido)-1-carboxypentyl] iminodiacetic acid, N-(5-aminopentyl)-iminodiacetic acid, and the like can be used.

Although no particular limitation is imposed on the binding site on the aforementioned sense strand RNA for a substituent, a functional molecule, or a linker connecting the substituent or functional molecule, they are preferably bound in such a way that they substitute a hydrogen atom constituting a hydroxyl group in the phosphate moiety of a certain nucleotide in the sense strand RNA.

The siRNA of the present invention is specifically exemplified by double-stranded RNA containing the sense sequences and the antisense sequences of (a) to (s) below.

TABLE 1

| siRNA No. | Target site base positions | Sense (5'→3') | SEQ ID NO | Anti-sense (5'→3') | SEQ ID NO |
|---|---|---|---|---|---|
| (a) | 1285 ~ 1305 | CCGAGAAGCGGUACCUGAACC | 2 | UUCAGGUACCGCUUCUCGGAG | 3 |
| (b) | 1298 ~ 1318 | CCUGAACCCGUGUUGCUCUCC | 4 | AGAGCAACACGGGUUCAGGUA | 5 |
| (c) | 1398 ~ 1418 | CCUGGCGAUACCUCAGCAACC | 6 | UUGCUGAGGUAUCGCCAGGAA | 7 |
| (d) | 1434 ~ 1454 | GCGACUCGCCAGAGUGGUUAU | 8 | AACCACUCUGGCGAGUCGCUG | 9 |
| (e) | 1435 ~ 1455 | CGACUCGCCAGAGUGGUUAUC | 10 | UAACCACUCUGGCGAGUCGCU | 11 |
| (f) | 1436 ~ 1456 | GACUCGCCAGAGUGGUUAUCU | 12 | AUAACCACUCUGGCGAGUCGC | 13 |
| (g) | 1438 ~ 1458 | CUCGCCAGAGUGGUUAUCUUU | 14 | AGAUAACCACUCUGGCGAGUC | 15 |
| (h) | 1440 ~ 1460 | CGCCAGAGUGGUUAUCUUUUG | 16 | AAAGAUAACCACUCUGGCGAG | 17 |
| (i) | 1441 ~ 1461 | GCCAGAGUGGUUAUCUUUUGA | 18 | AAAAGAUAACCACUCUGGCGA | 19 |
| (j) | 1443 ~ 1463 | CAGAGUGGUUAUCUUUUGAUG | 20 | UCAAAAGAUAACCACUCUGGC | 21 |
| (k) | 1548 ~ 1568 | GGGAUAACACACUGCAAGUGG | 22 | ACUUGCAGUGUGUUAUCCCUG | 23 |
| (l) | 1557 ~ 1577 | CACUGCAAGUGGACAUCAACG | 24 | UUGAUGUCCACUUGCAGUGUG | 25 |
| (s) | 1557 ~ 1579 | CACACUGCAAGUGGACAUCAACG | 54 | CGUUGAUGUCCACUUGCAGUGUG | 55 |
| (m) | 1608 ~ 1628 | CCACCAUUCAUGGCAUGAACC | 26 | UUCAUGCCAUGAAUGGUGGCC | 27 |
| (n) | 1700 ~ 1720 | GCCCUGGACACCAACUAUUGC | 28 | AAUAGUUGGUGUCCAGGGCUC | 29 |
| (o) | 1706 ~ 1726 | GACACCAACUAUUGCUUCAGC | 30 | UGAAGCAAUAGUUGGUGUCCA | 31 |
| (p) | 1778 ~ 1798 | GACCUCGGCUGGAAGUGGAUC | 32 | UCCACUUCCAGCCGAGGUCCU | 33 |
| (q) | 1806 ~ 1826 | CCAAGGGCUACCAUGCCAACU | 34 | UUGGCAUGGUAGCCCUUGGGC | 35 |
| (r) | 1887 ~ 1907 | CCCUGUACAACCAGCAUAACC | 36 | UUAUGCUGGUUGUACAGGGCC | 37 |

Also, preferred examples of the chimeric siRNA include one in which 1 to 8 nucleotides from the 3' terminus of the sense strand and 1 to 6 nucleotides from the 5' terminus of the antisense strand are consecutively converted into DNA in an arbitrary number. Examples of the preferred chimeric siRNA obtained using the aforementioned siRNA (1) are as follows.

In the table, capital letters, small letters, and underlines indicate RNA, DNA, and overhang positions, respectively.

Although no particular limitation is imposed on the production method of the siRNA of the present invention, it can be synthesized by a known production method, for example, in vitro chemical synthesis and transcriptional synthesis using promoters and RNA polymerases.

TABLE 2

| SiRNA No. | Sense (5' → 3') | SEQ ID NO | Anti-sense (5' → 3') | SEQ ID NO |
|---|---|---|---|---|
| (I-C8a) | CACUGCAAGUGGAcatcaacg | 38 | ttgatgUCCACUUGCAGUGUG | 39 |
| (I-C7) | CACUGCAAGUGGACatcaacg | 40 | ttgatGUCCACUUGCAGUGUG | 41 |
| (I-C6) | CACUGCAAGUGGACAtcaacg | 42 | ttgaUGUCCACUUGCAGUGUG | 43 |
| (I-C5) | CACUGCAAGUGGACAUcaacg | 44 | ttgAUGUCCACUUGCAGUGUG | 45 |
| (I-C4a) | CACUGCAAGUGGACAUCaacg | 46 | ttGAUGUCCACUUGCAGUGUG | 47 |
| (I-C3) | CACUGCAAGUGGACAUCAacg | 48 | tUGAUGUCCACUUGCAGUGUG | 49 |
| (I-C2) | CACUGCAAGUGGACAUCAAcg | 50 | UUGAUGUCCACUUGCAGUGUG | 25 |
| (I-C1) | CACUGCAAGUGGACAUCAAcg | 51 | UUGAUGUCCACUUGCAGUGUG | 25 |
| (I-C4b) | CACUGCAAGUGGACAUCaacg | 46 | UUGAUGUCCACUUGCAGUGtg | 56 |

Chemical synthesis can be performed by a nucleic acid synthesizer, using an amidite resin containing nucleic acid molecules, which are the constituent element of siRNA, as the raw material.

Transcriptional synthesis can be performed by in vitro transcription, which enables synthesis of double-stranded RNA by trimming hairpin RNA.

The siRNA of the present invention thus obtained can effectively inhibit the TGF-β1 expression in human alveolar epithelium-derived cells at the mRNA level, and further, exhibit an improving effect on the symptoms of pulmonary fibrosis in the lungs of a mouse model of pulmonary fibrosis without inducing the interferon reaction, as will be demonstrated later in Examples.

Accordingly, the siRNA of the present invention and an expression vector capable of expressing the siRNA in subjects administered with the vector are useful as a pharmaceutical for administration to a human or animal (pharmaceutical composition). Specifically, a pharmaceutical for the inhibition of the TGF-β1 gene expression, a pharmaceutical for preventing or treating a disease attributable to overexpression of TGF-β1 such as fibrosis, namely, a preventive or therapeutic agent for fibrosis.

Here, there is a variety of diseases that lead to fibril formation in the lungs, such as interstitial pneumonia, cystic fibrosis, chronic obstructive pulmonary disease (COPD), acute respiratory distress syndrome (ARDS), inflammatory lung disease, pulmonary infection, radiation pneumonitis, drug-induced interstitial pneumonia, and collagen disease-associated interstitial pneumonia; however, among idiopathic interstitial pneumonias (IIPs) of unidentified cause, idiopathic pulmonary fibrosis (IPF) is particularly preferable. As the clinicopathologic disease, IIPs include idiopathic pulmonary fibrosis (IPF), non-specific interstitial pneumonia (NSIP), cryptogenic organizing pneumonia (COP/BOOP), acute interstitial pneumonia (AIP), desquamative interstitial pneumonia (DIP), respiratory bronchiolitis-associated interstitial pneumonia (RB-ILD), lymphocytic interstitial pneumonia (LIP), and the like.

In addition, there are reports that TGF-β1 promotes cancer, in particular lung adenocarcinoma invasion and metastasis (Mol Cell Biochem (2011) 355:309-314, Cancer Genomics Proteomics 2010, 7, 217), TGF-β1 is overexpressed at sites of normal tissue injury after cancer therapy and the normal tissue injury can be prevented by targeting the TGF-β1 pathway (The oncologist 2010; 15: 350-359), etc. Accordingly, the siRNA of the present invention and an expression vector capable of expressing the siRNA in subjects administered with the vector are useful as a pharmaceutical for preventing or treating cancer, in particular lung cancer.

When using the siRNA of the present invention as a pharmaceutical, although it can be used as it is, it may also be allowed to form a complex with highly branched cyclic dextrin or cycloamylose. Here, highly branched cyclic dextrin refers to glucan with a degree of polymerization of 50 to 5000 having an inner branched cyclic structure moiety and an outer branched structure moiety, being produced by allowing branching enzymes to act on amylopectin. Here, the inner branched cyclic structure moiety refers to a cyclic structure moiety formed by an α-1,4-glucoside bond and an α-1,6-glucoside bond, and the outer branched structure moiety refers to a non-cyclic structure moiety bound to the inner branched cyclic structure moiety. Examples of preferred embodiments of the highly branched cyclic dextrin include one in which the degree of polymerization of the inner branched cyclic structure moiety of the aforementioned glucan is 10 to 100, one in which the degree of polymerization of the outer branched structure moiety of the aforementioned glucan is 40 or higher, and one in which an average degree of polymerization of each unit chain of the aforementioned outer branched structure moiety is 10 to 20. Also, highly branched cyclic dextrin is commercially available, and those commercial products can also be used for the present invention.

Cycloamylose is cyclic α-1,4-glucan, in which glucose units are linked by an α-1,4 linkage, and has a three-dimensional, deep hollow space within the helix structure. Although no particular limitation is imposed on the degree of polymerization of glucose in cycloamylose used for the present invention, for example, it is 10 to 500, preferably 10 to 100, and more preferably 22 to 50. Cycloamylose can be prepared from glucose using enzymes such as amylomaltase. Also, cycloamylose is commercially available, and those commercial products can also be used for the present invention (see WO2009/61003).

The siRNA of the present invention can be prepared as a pharmaceutical composition using one or more pharmaceutically acceptable carriers or diluents by an ordinary method. The pharmaceutical composition may be given via any administration route such as pulmonary administration, nasal administration, oral administration, rectal administration, and injection, and the administration may be systemic or local. The dosage form of the pharmaceutical composition may be any form suitable for use according to an administration route, such as a liquid, a suspension, an emulsion, a tablet, a pill, a pellet, a capsule, a powder, a sustained-release preparation, a suppository, an aerosol, and a spray.

For example, in nasal administration, the active ingredient is dissolved in an appropriate solvent (such as physiological saline and alcohol) and the resulting solution is injected or added dropwise to the nose, whereby the active ingredient can be delivered. Alternatively, in pulmonary administration or nasal administration, the active ingredient is sprayed with an aerosol from a pressurized pack or a nebulizer using an appropriate propellant such as dichlorodifluoromethane, trichlorofluoromethane, dichlorotetrafluoroethane, carbon dioxide, or other appropriate gases, whereby the active ingredient can be conveniently delivered. When using pressurized aerosol, the dosage unit can be fixed by providing a valve so that a measured amount is delivered. Further, the active ingredient can also be administered as a powder inhalant.

In the case of injections, for example, the active ingredient can be formulated as a solution for parenteral administration to be given by a bolus injection or continuous infusion (i.e., intravenous or intramuscular administration), and it is preferably formulated as a physiologically compatible buffer such as Hanks' solution, Ringer's solution, and physiological saline. This solution may contain medicinal agents which are allowed to be added such as suspending agents, stabilizers, and/or dispersants. Alternatively, the active ingredient can be prepared as a powder so that it is reconstructed with an appropriate diluent such as sterilized water not containing thermogenic substances before use. An injection preparation can be provided as, for example, a unit dosage form in an ampoule or a multi-dose container with preservatives.

For oral administration, the therapeutic agent of the present invention can be in the form of, for example, a tablet, a granule, a powder, an emulsion, a capsule, a syrup, an aqueous or oily suspension, or an elixir. In the case of a tablet or a pill, the composition can be coated in order to delay dispersion and absorption in the gastrointestinal tract so that a long-lasting action is obtained.

Although no limitation is imposed on the pharmaceutically acceptable carrier or diluent, examples thereof include liquids (such as water, oil, physiological saline, an aqueous solution of dextrose, and ethanol) and solids (such as acacia gum, gelatin, starch, glucose, lactose, sucrose, talc, sodium stearate, glycerol monostearate, keratin, colloidal silica, dried skim milk, and glycerol). Also, the therapeutic agent of the present invention may contain an appropriate agent which is added to ordinary pharmaceutical compositions such as an aid, an antiseptic, a stabilizer, a thickening agent, a lubricant, a colorant, a wetting agent, an emulsifier, and a pH buffer.

The pharmaceutical composition of the present invention can contain the siRNA of the present invention in an amount of 0.001 to 50 mass %, preferably 0.01 to 10 mass %, and more preferably 0.1 to 1 mass %.

Although the dose of the pharmaceutical composition of the present invention is not particularly limited as long as the effective amount is applied, for example, it is preferably 0.0001 to 100 mg, and more preferably 0.002 to 1 mg per kg body weight.

EXAMPLES

Hereinbelow, the present invention will be described in more detail with reference to Examples. However, the technical scope of the present invention is not limited to these Examples.

Example 1

Production of siRNA

The siRNA molecules targeting the TGF-β1 gene as shown in Table 3 below were designed and each siRNA oligonucleotide was chemically synthesized. The resulting oligonucleotides were purified by HPLC before use.

TABLE 3

| siRNA No. | Target site base positions | Sense (5'→3') | SEQ ID NO | Anti-sense (5'→3') | SEQ ID NO |
|---|---|---|---|---|---|
| (a) | 1285 ~ 1305 | CCGAGAAGCGGUACCUGAACC | 2 | UUCAGGUACCGCUUCUCGGAG | 3 |
| (b) | 1298 ~ 1318 | CCUGAACCCGUGUUGCUCUCC | 4 | AGAGCAACACGGGUUCAGGUA | 5 |
| (c) | 1398 ~ 1418 | CCUGGCGAUACCUCAGCAACC | 6 | UUGCUGAGGUAUCGCCAGGAA | 7 |
| (d) | 1434 ~ 1454 | GCGACUCGCCAGAGUGGUUAU | 8 | AACCACUCUGGCGAGUCGCUG | 9 |
| (e) | 1435 ~ 1455 | CGACUCGCCAGAGUGGUUAUC | 10 | UAACCACUCUGGCGAGUCGCU | 11 |
| (f) | 1436 ~ 1456 | GACUCGCCAGAGUGGUUAUCU | 12 | AUAACCACUCUGGCGAGUCGC | 13 |
| (g) | 1438 ~ 1458 | CUCGCCAGAGUGGUUAUCUUU | 14 | AGAUAACCACUCUGGCGAGUC | 15 |
| (h) | 1440 ~ 1460 | cGCCAGAGUGGUUAUCUUUUG | 16 | AAAGAUAACCACUCUGGCGAG | 17 |
| (i) | 1441 ~ 1461 | GCCAGAGUGGUUAUCUUUUGA | 18 | AAAAGAUAACCACUCUGGCGA | 19 |
| (j) | 1443 ~ 1463 | CAGAGUGGUUAUCUUUUGAUG | 20 | UCAAAAGAUAACCACUCUGGC | 21 |
| (k) | 1548 ~ 1568 | GGGAUAACACACUGCAAGUGG | 22 | ACUUGCAGUGUGUUAUCCCUG | 23 |
| (l) | 1557 ~ 1577 | CACUGCAAGUGGACAUCAACG | 24 | UUGAUGUCCACUUGCAGUGUG | 25 |
| (s) | 1557 ~ 1579 | CACACUGCAAGUGGACAUCAACG | 54 | CGUUGAUGUCCACUUGCAGUGUG | 55 |
| (m) | 1608 ~ 1628 | CCACCAUUCAUGGCAUGAACC | 26 | UUCAUGCCAUGAAUGGUGGCC | 27 |
| (n) | 1700 ~ 1720 | GCCCUGGACACCAACUAUUGC | 28 | AAUAGUUGGUGUCCAGGGCUC | 29 |
| (o) | 1706 ~ 1726 | GACACCAACUAUUGCUUCAGC | 30 | UGAAGCAAUAGUUGGUGUCCA | 31 |
| (p) | 1778 ~ 1798 | GACCUCGGCUGGAAGUGGAUC | 32 | UCCACUUCCAGCCGAGGUCCU | 33 |
| (q) | 1806 ~ 1826 | CCAAGGGCUACCAUGCCAACU | 34 | UUGGCAUGGUAGCCCUUGGGC | 35 |
| (r) | 1887 ~ 1907 | CCCUGUACAACCAGCAUAACC | 36 | UUAUGCUGGUUGUACAGGGCC | 37 |

For the pharmaceutical composition of the present invention, in place of the siRNA of the present invention, an expression vector capable of expressing the siRNA in a subject administered with the vector can also be used.

In this case, the expression vector can be constructed by, for example, inserting DNA capable of encoding the siRNA of the present invention into an appropriate vector used for gene therapy such as an adenovirus vector, an adeno-associated virus vector (AAV), or a lentivirus vector.

Example 2

Evaluation of Inhibitory Effect on TGF-β1 Expression (In Vitro)

(1) Cell
Human alveolar epithelium-derived A549 cells (DS Pharma Biomedical Co., Ltd.) were used.
(2) Culture Conditions
Using Dulbecco's modified Eagle's Medium (D-MEM) containing 10% fetal bovine serum (with 100 unit/mL penicillin and 100 µg/mL streptomycin), 1×10⁵ cells were seeded in a 12-well plate. After culturing under the conditions of 37° C. and 5% $CO_2$ overnight, the A549 cells were 40% confluent, and the medium was replaced with a serum-free medium.

(3) Pre-Treatment and the Addition Amount of siRNA

As siRNA, oligonucleotides shown in Table 3 above were used, and when the cells reached 40% confluence, the oligonucleotides were introduced into the aforementioned cells using Lipofectamine 2000 (Invitrogen).

Specifically, 2.0 µL of Lipofectamine 2000 was added to 98 µL of OPTI-MEM (Invitrogen) per well, and the resulting mixture was incubated at room temperature for five minutes (solution A).

To 99.375 µL of OPTI-MEM, 0.625 µL of a 0.2 µM siRNA solution was added (solution B). Solutions A and B were mixed and incubated at room temperature for 20 minutes. After incubation, the AB mixture was added to each well of the 12-well plate. The siRNA was added so that the final concentration was 0.1 nM.

(4) Post-Treatment (i) Cytokine Treatment

Six hours after addition of the mixed solution of siRNA and Lipofectamine, the medium was replaced with D-MEM medium containing 0.1% bovine serum albumin (BSA) and cytokine (1 ng/mL IL-1β and 1 ng/mL TNF-α), followed by culturing for 12 hours. After culturing, the culture supernatants were sampled.

(ii) Extraction of Total Cellular RNA

For extraction of total cellular RNA, an automated nucleic acid extraction apparatus QuickGene-810 (Fujifilm Corporation) and QuickGene RNA cultured cell kit S (Fujifilm Corporation), which was an exclusive kit for QuickGene-810, were used. The cells were washed with 1.0 mL of PBS, to which 0.5 mL of a cell lysis solution was added to extract the total cellular RNA. After addition of 0.5 mL of the lysis solution (LRC, mercapto ethanol was already added) to the 12-well plate, the plate was stirred on a see-saw shaker for five minutes. The solution was mixed well by pipetting five to six times, and then transferred to an Eppendorf tube. To the Eppendorf tube, 420 µL of ethanol was added, and the resulting mixture was stirred on a vortex mixer for 15 seconds and then processed in QuickGene-810. During processing in QuickGene-810, DNase (RQ1 RNase-free DNase, Promega Corporation) was added. The samples of the total RNA thus extracted were stored in a refrigerator at −80° C. until the subsequent processing.

(iii) Conversion of the Total RNA into cDNA

The RNA concentrations (µg/mL) in the samples of the total RNA extracted from the cultured cells were calculated from the absorption value measured at 260 nm (control: TE buffer). Based on the values thus obtained, the solution of each sample was placed in a 96-well plate in such an amount that the amount of RNA was 0.1 µg. To each well, distilled water was added to bring the total volume to 12 µL, and further, 2 µL of gDNA Wipeout Buffer included in the QuantiTect Reverse Transcription Kit (QIAGEN) was added. After mixing with a vortex, the samples were incubated at 42° C. for two minutes, and then cooled at 4° C. To these samples, 1 µL of Quantiscript Reverse Transcriptase, 4 µL of Quantiscript RT Buffer, and 1 µL of RT Primer Mix included in the QuantiTect Reverse Transcription Kit (QIAGEN) were added, followed by mixing and incubation at 42° C. for 15 minutes. Subsequently, the samples were heated at 95° C. for three minutes to inactivate Quantiscript Reverse Transcriptase, and then cooled at 4° C.

The solution thus prepared (i.e., an undiluted cDNA preparation solution) was diluted 5-fold with a TE buffer and served as a cDNA solution for PCR targeting the target gene (TGF-β1).

Also, the undiluted cDNA preparation solution was diluted 50-fold with a TE buffer and served as a cDNA solution for PCR targeting GAPDH, which was selected as an internal reference gene. It should be noted that an undiluted cDNA preparation solution of a control sample (i.e., non-siRNA administration) was diluted 1-, 10-, 100-, and 1000-fold with a TE buffer and served as a sample to construct a calibration curve for PCR targeting TGF-β1. Likewise, the undiluted cDNA preparation solution of a control sample was diluted 10-, 100-, 1000-, and 10000-fold with a TE buffer and served as a sample to construct a calibration curve for PCR targeting GAPDH.

(5) Method for Measuring the Expression Level of TGF-β1

To 2.5 µL of a TGF-β1-derived cDNA product, which was used as a template, 12.5 µL of QuantiFast SYBR Green PCR Master Mix (QIAGEN) and 2.5 µL of QuantiTect Primer Assay (QIAGEN) for human-derived TGF-β1 gene or human-derived GAPDH gene were added. To the solution, sterilized distilled water was added to bring the final volume to 25 µL, whereby a PCR reaction solution was prepared. Then, using Applied Biosystems 7500 (Life Technologies Japan Ltd.), the solution thus prepared was heated at 95° C. for five minutes and then subjected to 40 cycles of PCR, where one cycle included 1)95°) C. for 10 seconds and 2) 60° C. for 35 seconds, followed by gradual cooling from 95° C. to 60° C. The resulting solution was subjected to thermal dissociation measurement. Based on the threshold cycle (Ct) value derived from PCR amplification process, the rate of amplification of each target gene was corrected based on the Ct value of GAPDH gene, and the inhibitory effect on mRNA of a target gene was evaluated. The results thus obtained are shown in FIG. 1 and Table 4.

TABLE 4

| siRNA | | Rate of TGF-β1 mRNA expression (TGF-β1/GAPDH) | |
|---|---|---|---|
| No. | nM | Mean | SD |
| a | 0.1 | 24.7 | 7.6 |
| b | 0.1 | 85 | 8.9 |
| c | 0.1 | 51.8 | 12.3 |
| d | 0.1 | 58.5 | 6.4 |
| e | 0.1 | 27.5 | 2.2 |
| f | 0.1 | 52.1 | 4.1 |
| g | 0.1 | 51.8 | 7.5 |
| h | 0.1 | 29.3 | 8.6 |
| i | 0.1 | 31.5 | 12.5 |
| j | 0.1 | 40.1 | 6.9 |
| k | 0.1 | 22.2 | 6.6 |
| l | 0.1 | 12.2 | 6.7 |
| s | 1 | 50.1 | 4.3 |
| m | 0.1 | 71.6 | 10.4 |
| n | 0.1 | 39.7 | 4.7 |
| o | 0.1 | 11.7 | 3.1 |
| p | 0.1 | 55.5 | 4.4 |
| q | 0.1 | 51.3 | 4.4 |
| r | 0.1 | 53.4 | 7.8 |

The siRNAs having siRNA numbers of d, p, r, f, c, g, q, j, n, i, h, e, a, k, l, and o were found to have an inhibition efficiency on the TGF-β1 expression of 40% or higher even at a concentration of 0.1 nM. Particularly, siRNAs having siRNA numbers of l and o exhibited an inhibition efficiency of 80% or higher even at 0.1 nM. Further, these sequences exhibited remarkable inhibitory effects also at 0.01 nM.

Example 3

Production of Chimeric siRNA

Based on the siRNA number (1), chimeric siRNA molecules targeting the TGF-β1 gene as shown in Table 5 below were designed and each chimeric siRNA oligonucleotide was chemically synthesized. The resulting oligonucleotides were purified by HPLC before use.

TABLE 5

| siRNA No. | Sense (5' → 3') | SEQ ID NO | Anti-sense (5' → 3') | SEQ ID NO |
|---|---|---|---|---|
| (I-C8a) | CACUGCAAGUGGAcatcaacg | 38 | ttgatgUCCACUUGCAGUGUG | 39 |
| (I-C7) | CACUGCAAGUGGACatcaacg | 40 | ttgatGUCCACUUGCAGUGUG | 41 |
| (I-C6) | CACUGCAAGUGGACAtcaacg | 42 | ttgaUGUCCACUUGCAGUGUG | 43 |
| (I-C5) | CACUGCAAGUGGACAUcaacg | 44 | ttgAUGUCCACUUGCAGUGUG | 45 |
| (I-C4a) | CACUGCAAGUGGACAUCaacg | 46 | ttGAUGUCCACUUGCAGUGUG | 47 |
| (I-C3) | CACUGCAAGUGGACAUCAacg | 48 | tUGAUGUCCACUUGCAGUGUG | 49 |
| (I-C2) | CACUGCAAGUGGACAUCAAcg | 50 | UUGAUGUCCACUUGCAGUGUG | 25 |
| (I-C1) | CACUGCAAGUGGACAUCAAcg | 51 | UUGAUGUCCACUUGCAGUGUG | 25 |
| (I-C4b) | CACUGCAAGUGGACAUCaacg | 46 | UUGAUGUCCACUUGCAGUGtg | 56 |

In the table, capital letters, small letters, and underlines indicate RNA, DNA, and overhang positions, respectively.

Example 4

Evaluation of Inhibitory Effect on TGF-β1 Expression

Figure 2:
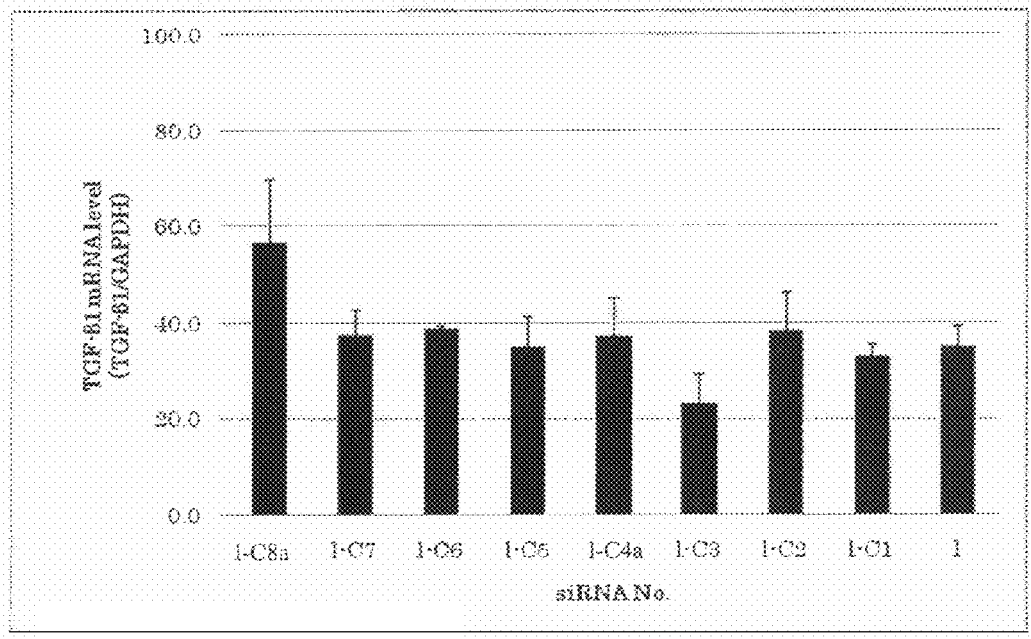
FIG. 2 is a graph showing the rate of inhibition of the expression of TGF-β1 mRNA by chimeric siRNA.

Using the oligonucleotides shown in Table 5 (concentration: 10 nM or 0.1 nM), the inhibitory effect on the TGF-β1 expression was evaluated by a similar method to that in Example 2. The results are shown in FIG. 2 and Table 6.

TABLE 6

| siRNA No. | nM | Rate of TGF-β1 mRNA expression (TGF-β1/GAPDH) Mean | SD |
|---|---|---|---|
| 1 | 10 | 34.9 | 4.2 |
| 1-C8a | 10 | 56.6 | 13.2 |
| 1-C7 | 10 | 37.5 | 5.1 |
| 1-C6 | 10 | 38.8 | 0.5 |

TABLE 6-continued

| siRNA No. | nM | Rate of TGF-β1 mRNA expression (TGF-β1/GAPDH) Mean | SD |
|---|---|---|---|
| 1-C5 | 10 | 35.1 | 6.2 |
| 1-C4a | 10 | 37.2 | 8.0 |
| 1-C3 | 10 | 23.0 | 6.3 |
| 1-C2 | 10 | 38.4 | 7.9 |
| 1-C1 | 10 | 33.0 | 2.5 |
| 1-C4b | 0.1 | 69.9 | 4.3 |

Example 5

Synthesis of Phosphate- or Thiophosphate-Bound Chimeric siRNA

Based on the siRNA number (1), phosphate- or thiophosphate-bound chimeric siRNA molecules targeting the TGF-β1 gene as shown in Table 7 below were designed and each chimeric siRNA oligonucleotide was chemically synthesized. The resulting oligonucleotides were purified by HPLC before use.

TABLE 7

| siRNA No. | Sense (5' → 3') | SEQ ID NO | Anti-sense (5' → 3') | SEQ ID NO |
|---|---|---|---|---|
| (I-CP8a) | CACUGCAAGUGGAcatcaacg | 38 | P-ttgatgUCCACUUGCAGUGUG | 39 |
| (I-CP7) | CACUGCAAGUGGACatcaacg | 40 | P-ttgatGUCCACUUGCAGUGUG | 41 |
| (I-CP6) | CACUGCAAGUGGACAtcaacg | 42 | P-ttgaUGUCCACUUGCAGUGUG | 43 |
| (I-CP5) | CACUGCAAGUGGACAUcaacg | 44 | P-ttgAUGUCCACUUGCAGUGUG | 45 |
| (I-CP4a) | CACUGCAAGUGGACAUCaacg | 46 | P-ttGAUGUCCACUUGCAGUGUG | 47 |
| (I-CP3a) | CACUGCAAGUGGACAUCAacg | 48 | P-tUGAUGUCCACUUGCAGUGUG | 49 |
| (I-CP2) | CACUGCAAGUGGACAUCAAcg | 50 | P-UUGAUGUCCACUUGCAGUGUG | 25 |
| (I-CP1) | CACUGCAAGUGGACAUCAACg | 51 | P-UUGAUGUCCACUUGCAGUGUG | 25 |
| (I-CP) | CACUGCAAGUGGACAUCAACG | 24 | P-UUGAUGUCCACUUGCAGUGUG | 25 |
| (I-CP8b) | CACUGCAAGUGGAcatcaacg | 38 | P-UUGAUGUCCACUUGCAGUGtg | 56 |
| (I-CP4b) | CACUGCAAGUGGACAUCaacg | 46 | P-UUGAUGUCCACUUGCAGUGtg | 56 |

TABLE 7-continued

| siRNA No. | Sense (5' → 3') | SEQ ID NO | Anti-sense(5' → 3') | SEQ ID NO |
|---|---|---|---|---|
| (I-CPS4b) | CACUGCAAGUGGACAUCaacg | 46 | PS-UUGAUGUCCACUUGCAGUGtg | 56 |
| (I-CP3b) | CACUGCAAGUGGACAUCAkcg | 57 | P-UUGAUGUCCACUUGCAGUGtg | 56 |

In the table, capital letters, small letters, and underlines indicate RNA, DNA, and overhang positions, respectively. Also, P- and PS-indicate 5'-terminal phosphorylation and 5'-terminal thiophosphorylation, respectively.

Example 6

Evaluation of Inhibitory Effect on TGF-β1 Expression

Figure 3:
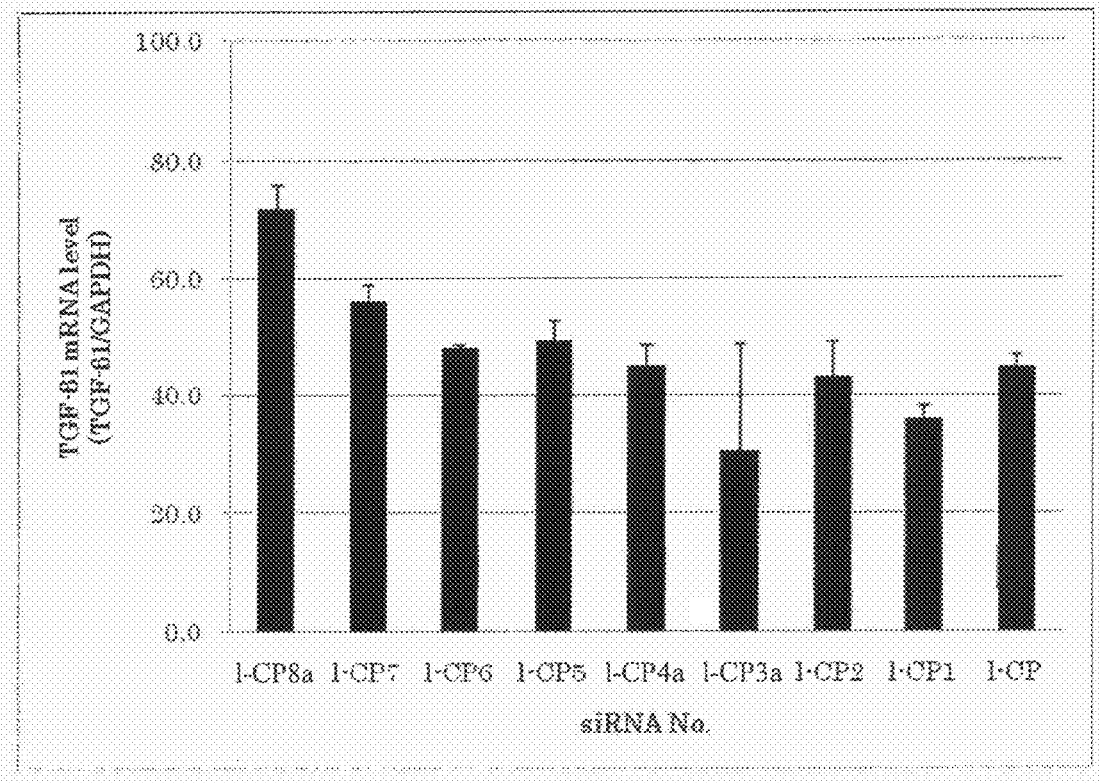
FIG. 3 is a graph showing the rate of inhibition of the expression of TGF-β1 mRNA by phosphate- or thiophosphate-linked chimeric siRNA.

Using the oligonucleotides shown in Table 7, the inhibitory effect on the TGF-β1 expression was evaluated by a similar method to that in Example 2. The results are shown in FIG. 3 and Table 8.

TABLE 8

| siRNA | | Rate of TGF-β1 mRNA expression (TGF-β1/GAPDH) | |
|---|---|---|---|
| No. | nM | Mean | SD |
| 1-CP8a | 0.1 | 72.0 | 3.8 |
| 1-CP7 | 0.1 | 56.1 | 2.7 |
| 1-CP6 | 0.1 | 48.2 | 0.4 |
| 1-CP5 | 0.1 | 49.4 | 3.4 |

TABLE 8-continued

| siRNA | | Rate of TGF-β1 mRNA expression (TGF-β1/GAPDH) | |
|---|---|---|---|
| No. | nM | Mean | SD |
| 1-CP4a | 0.1 | 45.1 | 3.6 |
| 1-CP3a | 0.1 | 30.6 | 18.2 |
| 1-CP2 | 0.1 | 43.1 | 6.1 |
| 1-CP1 | 0.1 | 36.1 | 2.0 |
| 1-CP | 0.1 | 44.9 | 2.0 |
| 1-CP8b | 0.1 | 57.1 | 12.4 |
| 1-CP4b | 0.1 | 46.4 | 17.4 |
| 1-CPS4b | 0.1 | 70.8 | 2.2 |
| 1-CP3b | 0.1 | 42.1 | 2.9 |

Example 7

Synthesis of siRNA Having DNA in its Overhang Portion

Based on the siRNA number (1), siRNA molecules having DNA in the overhang portion and targeting the TGF-β1 gene as shown in Table 9 below were designed and each siRNA oligonucleotide was chemically synthesized. The resulting oligonucleotides were purified by HPLC before use.

TABLE 9

| siRNA No. | Sense (5' → 3') | SEQ ID NO | Antisense (5' → 3') | SEQ ID NO |
|---|---|---|---|---|
| I-OHa1 | CACUGCAAGUGGACAUCAACGt | 58 | UUGAUGUCCACUUGCAGUGUG | 25 |
| I-OHa2 | CACUGCAAGUGGACAUCAACGtt | 59 | UUGAUGUCCACUUGCAGUGUG | 25 |
| I-OHa3 | CACUGCAAGUGGACAUCAACGttt | 60 | UUGAUGUCCACUUGCAGUGUG | 25 |
| I-OHa4 | CACUGCAAGUGGACAUCAACGtttt | 61 | UUGAUGUCCACUUGCAGUGUG | 25 |
| I-OHa5 | CACUGCAAGUGGACAUCAACGttttt | 62 | UUGAUGUCCACUUGCAGUGUG | 25 |
| I-OHa6 | CACUGCAAGUGGACAUCAACGtttttt | 63 | UUGAUGUCCACUUGCAGUGUG | 25 |
| I-OHa7 | CACUGCAAGUGGACAUCAACGttttttt | 64 | UUGAUGUCCACUUGCAGUGUG | 25 |
| I-OHb1 | CACUGCAAGUGGACAUCAACGta | 65 | UUGAUGUCCACUUGCAGUGUG | 25 |
| I-OHb2 | CACUGCAAGUGGACAUCAACGttaa | 66 | UUGAUGUCCACUUGCAGUGUG | 25 |
| I-OHb3 | CACUGCAAGUGGACAUCAACGtttaaa | 67 | UUGAUGUCCACUUGCAGUGUG | 25 |
| I-OHb4 | CACUGCAAGUGGACAUCAACGttttaaaa | 68 | UUGAUGUCCACUUGCAGUGUG | 25 |
| I-OHb5 | CACUGCAAGUGGAcatcaacgtta | 69 | ttgatgUCCACUUGCAGUGUG | 39 |
| I-OHb6 | CACUGCAAGUGGAcatcaacgtttaaa | 70 | ttgatgUCCACUUGCAGUGUG | 39 |

In the table, capital letters, small letters, and underlines indicate RNA, DNA, and overhang positions, respectively.

Example 8

Evaluation of Inhibitory Effect on TGF-β1 Expression

Using the oligonucleotides shown in Table 9, the inhibitory effect on the TGF-β1 expression was evaluated by a similar method to that in Example 2. The results are shown in Table 10.

TABLE 10

| siRNA | | Rate of TGF-β1 mRNA expression (TGF-β1/GAPDH) | |
|---|---|---|---|
| No. | nM | Mean | SD |
| 1-OHa1 | 0.1 | 26.0 | 1.0 |
| 1-OHa2 | 0.1 | 34.0 | 6.2 |
| 1-OHa3 | 0.1 | 32.8 | 3.8 |
| 1-OHa4 | 0.1 | 25.4 | 1.9 |
| 1-OHa5 | 0.1 | 27.4 | 1.5 |
| 1-OHa6 | 0.1 | 40.1 | 6.2 |
| 1-OHa7 | 1.0 | 39.7 | 22.6 |
| 1-OHb1 | 1 | 24.9 | 1.7 |
| 1-OHb2 | 1 | 25.6 | 0.9 |
| 1-OHb3 | 1 | 22.8 | 3.5 |
| 1-OHb4 | 1 | 20.4 | 1.5 |
| 1-OHb5 | 1 | 48.6 | 7.6 |
| 1-OHb6 | 1 | 46.6 | 6.7 |

Example 9

Evaluation of Efficacy in a Pulmonary Fibrosis Model (In Vivo Study)

Based on the siRNA number (q) (SEQ ID NOs: 34 and 35), which is a sequence shared between mice and humans, chimeric siRNA (q-C8: sense strand (5'→3'): CCAAGGGC-UACCAtgccaact (SEQ ID NO: 52), antisense strand (5'→+3'): ttggcaUGGUAGCCCUUGGGC (SEQ ID NO: 53) were designed, and in a similar manner to that in Example 3, chimeric siRNA oligonucleotides were synthesized and then purified by HPLC. Using the resulting chimeric siRNA oligonucleotides as test substances, efficacy in a mouse model of bleomycin-induced pulmonary fibrosis was evaluated.

After intraperitoneal administration of pentobarbital (the product of Dainippon Sumitomo Pharma Co., Ltd.) to mice (C57BL/6NCrSlc (SLC), female, 13-week-old), ALZET™ osmotic pumps (model 2001, DURECT Corporation) were implanted under the back skin of the mice under anesthesia to produce pulmonary fibrosis model mice. It is to be noted that 200 μL of an approximately 10 mg/mL solution of bleomycin in physiological saline was infused into the ALZET™ osmotic pump in advance, and for bleomycin, the product of Nippon Kayaku Co., Ltd. was used.

Three, seven, and 14 days after implantation of the ALZET™ osmotic pump, the test substances were dissolved in distilled water (the product of Otsuka Pharmaceutical Co., Ltd.) and intratracheally administered using MicroSprayer™ (model IA-1C, Penn-Century, Inc.) at a dose of 100 μg/body. The dose volumes were 75 μL/body on days 3 and 7, and 50 μL/body on day 14 after initiation of the bleomycin administration.

Also, as the comparative control, a group in which 200 μL of only physiological saline was infused into the ALZET™ osmotic pump and distilled water was administered as a test substance, and a group in which 200 μL of an approximately 10 mg/mL solution of bleomycin in physiological saline was infused into the ALZET™ osmotic pump and distilled water was administered as a test substance were prepared.

Twenty one days after implantation of the ALZET™ osmotic pump, pentobarbital was intraperitoneally administered to the mice, and under anesthesia, the skin and muscle of the neck were removed to expose the trachea. The mice were sacrificed by exsanguination via the jugular vein, and subsequently, using an indwelling needle, 2 mL of physiological saline (Otsuka Pharmaceutical Co., Ltd.) was infused into the trachea in three divided doses, and approximately 2 mL of bronchoalveolar lavage fluid (BALF) was collected. Subsequently, the chest was cut open and an incision was made in the left auricle, and approximately 1 mL of physiological saline was perfused from the right ventricle, and the lungs were excised. For histological evaluation, the left lobe of the excised lungs was immersed in a 10% formalin neutral buffer fixation solution (Wako Pure Chemical Industries, Ltd.).

Figure 4:
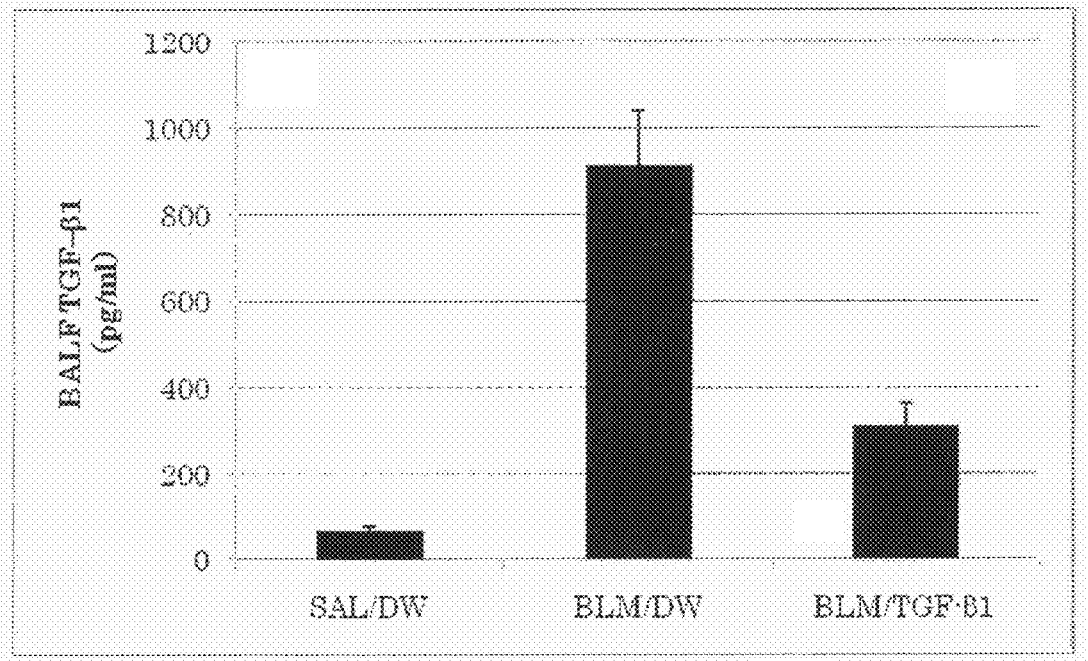
FIG. 4 is a graph showing the rate of inhibition of the TGF-β1 expression in a pulmonary fibrosis model.

The BALF thus collected was centrifuged (2000 rpm, 4° C., for 10 minutes), and the amount of TGF-β1 protein in the supernatant was measured by ELISA. The results are shown in FIG. 4. In the FIG. 4, SAL, DW, and BLM represent saline, distilled water, and bleomycin, respectively.

Figure 5:
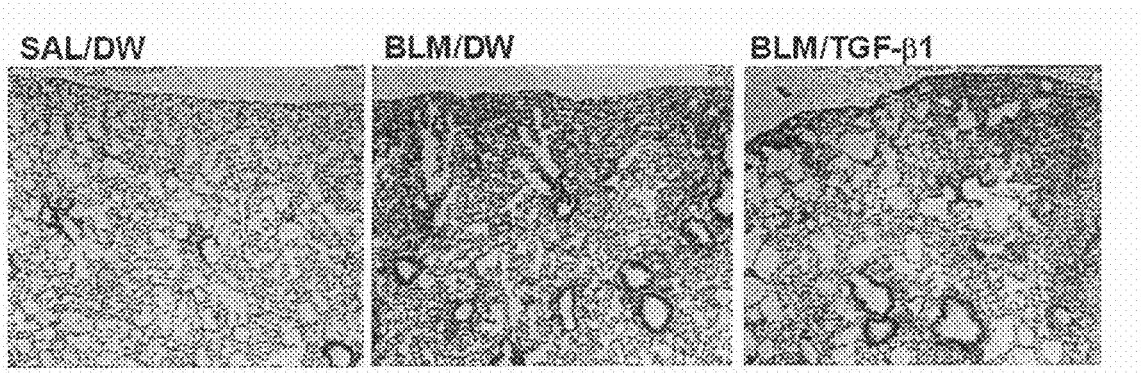
FIG. 5 is an optical microscopic picture of lung tissue sections (H.E. staining and Masson's trichrome staining) (magnification: 5×).

The lung tissue fixed with a 10% formalin neutral buffer fixation solution was embedded in paraffin and tissue sections were prepared, which were subjected to Hematoxilin-Eosin (H.E.) staining and Masson's trichrome staining. The tissue diagram is shown in FIG. 5.

From FIG. 4, in the test substance-administration group (BLM/TGF-β1), the amount of TGF-β1 in BALF was found to be remarkably decreased. This effect was not observed in the distilled water-administration group (BLM/DW) as a comparative control. Also, from the tissue diagram of FIG. 5, it was found that the degrees of inflammation and fibril formation were reduced in the test substance-administration group.

The invention claimed is:

1. A method for preventing or treating a disease that leads to fibril formation in the lungs, the method comprising:
    administering an effective amount of an siRNA to a human or animal in need thereof, wherein the siRNA has a full length of 30 or fewer nucleotides and selected from the group consisting of
    an siRNA comprising a sense sequence of SEQ ID NO: 2 and an antisense sequence of SEQ ID NO: 3;
    an siRNA comprising a sense sequence of SEQ ID NO: 4 and an antisense sequence of SEQ ID NO: 5;
    an siRNA comprising a sense sequence of SEQ ID NO: 6 and an antisense sequence of SEQ ID NO: 7;
    an siRNA comprising a sense sequence of SEQ ID NO: 8 and an antisense sequence of SEQ ID NO: 9;
    an siRNA comprising a sense sequence of SEQ ID NO: 10 and an antisense sequence of SEQ ID NO: 11;
    an siRNA comprising a sense sequence of SEQ ID NO: 12 and an antisense sequence of SEQ ID NO: 13;
    an siRNA comprising a sense sequence of SEQ ID NO: 16 and an antisense sequence of SEQ ID NO: 17;
    an siRNA comprising a sense sequence of SEQ ID NO: 18 and an antisense sequence of SEQ ID NO: 19;
    an siRNA comprising a sense sequence of SEQ ID NO: 20 and an antisense sequence of SEQ ID NO: 21;
    an siRNA comprising a sense sequence of SEQ ID NO: 22 and an antisense sequence of SEQ ID NO: 23;
    an siRNA comprising a sense sequence of SEQ ID NO: 24 and an antisense sequence of SEQ ID NO: 25;
    an siRNA comprising a sense sequence of SEQ ID NO: 26 and an antisense sequence of SEQ ID NO: 27;
    an siRNA comprising a sense sequence of SEQ ID NO: 28 and an antisense sequence of SEQ ID NO: 29;
    an siRNA comprising a sense sequence of SEQ ID NO: 30 and an antisense sequence of SEQ ID NO: 31;
    an siRNA comprising a sense sequence of SEQ ID NO: 32 and an antisense sequence of SEQ ID NO: 33;
    an siRNA comprising a sense sequence of SEQ ID NO: 36 and an antisense sequence of SEQ ID NO: 37;
    an siRNA comprising a sense sequence of SEQ ID NO: 54 and an antisense sequence of SEQ ID NO: 55,
    a variant thereof comprising a substitution, addition or deletion of one or several bases, and
    a variant thereof comprising a nucleotide analog chemically modified with a sugar, base and/or phosphate.

2. The method according to claim 1, wherein the disease that leads to fibril formation in the lungs is a disease selected from the group consisting of interstitial pneumonia, cystic fibrosis, chronic obstructive pulmonary disease (COPD), acute respiratory distress syndrome (ARDS), inflammatory lung disease, pulmonary infection, radiation pneumonitis, drug-induced interstitial pneumonia, collagen disease-associated interstitial pneumonia, and cancer.

3. The method according to claim 1, wherein the siRNA is the variant thereof comprising the substitution, addition, or deletion of one or several bases.

4. The method according to claim 1, wherein the siRNA is the variant thereof comprising a nucleotide analog having chemically modified sugar, base, and/or phosphate.

5. The method according to claim 1, wherein 1 to 10 consecutive nucleotides excluding an overhang nucleotide from a 3' terminus of a sense strand of the siRNA are converted into DNA.

6. The method according to claim 1, wherein 1 to 10 consecutive nucleotides from a 5' terminus of an antisense strand of the siRNA are converted into DNA.

7. The method according to claim 1, wherein 1 to 10 consecutive nucleotides excluding an overhang nucleotide from a 3' terminus of a sense strand of the siRNA are converted into DNA and 1 to 10 consecutive nucleotides from a 5' terminus of an antisense strand of the siRNA are converted into DNA.

8. The method according to claim 1, wherein a 5' terminus of an antisense strand is monophosphorylated.

9. The method according to claim 1, wherein a 5' terminus of an antisense strand is monothiophosphorylated.

10. A method for treating or preventing pulmonary fibrosis or lung cancer, the method comprising:
    administering an effective amount of an siRNA to a human or animal in need thereof, wherein the siRNA has a full length of 30 or fewer nucleotides and selected from the group consisting of
    an siRNA comprising a sense sequence of SEQ ID NO: 2 and an antisense sequence of SEQ ID NO: 3;
    an siRNA comprising a sense sequence of SEQ ID NO: 4 and an antisense sequence of SEQ ID NO: 5;
    an siRNA comprising a sense sequence of SEQ ID NO: 6 and an antisense sequence of SEQ ID NO: 7;
    an siRNA comprising a sense sequence of SEQ ID NO: 8 and an antisense sequence of SEQ ID NO: 9;
    an siRNA comprising a sense sequence of SEQ ID NO: 10 and an antisense sequence of SEQ ID NO: 11;
    an siRNA comprising a sense sequence of SEQ ID NO: 12 and an antisense sequence of SEQ ID NO: 13;
    an siRNA comprising a sense sequence of SEQ ID NO: 16 and an antisense sequence of SEQ ID NO: 17;
    an siRNA comprising a sense sequence of SEQ ID NO: 18 and an antisense sequence of SEQ ID NO: 19;
    an siRNA comprising a sense sequence of SEQ ID NO: 20 and an antisense sequence of SEQ ID NO: 21;
    an siRNA comprising a sense sequence of SEQ ID NO: 22 and an antisense sequence of SEQ ID NO: 23;
    an siRNA comprising a sense sequence of SEQ ID NO: 24 and an antisense sequence of SEQ ID NO: 25;
    an siRNA comprising a sense sequence of SEQ ID NO: 26 and an antisense sequence of SEQ ID NO: 27;
    an siRNA comprising a sense sequence of SEQ ID NO: 28 and an antisense sequence of SEQ ID NO: 29;
    an siRNA comprising a sense sequence of SEQ ID NO: 30 and an antisense sequence of SEQ ID NO: 31;
    an siRNA comprising a sense sequence of SEQ ID NO: 32 and an antisense sequence of SEQ ID NO: 33;
    an siRNA comprising a sense sequence of SEQ ID NO: 36 and an antisense sequence of SEQ ID NO: 37;
    an siRNA comprising a sense sequence of SEQ ID NO: 54 and an antisense sequence of SEQ ID NO: 55,
    a variant thereof comprising a substitution, addition or deletion of one or several bases, and
    a variant thereof comprising a nucleotide analog chemically modified with a sugar, base and/or phosphate.

11. The method of claim 10, which is to treat pulmonary fibrosis.

12. The method of claim 11, wherein the pulmonary fibrosis is idiopathic pulmonary fibrosis.

13. The method according to claim 10, wherein the siRNA is the variant thereof comprising the substitution, addition, or deletion of one or several bases.

14. The method according to claim 10, wherein the siRNA is the variant thereof comprising a nucleotide analog having chemically modified sugar, base, and/or phosphate.

15. The method according to claim 10, wherein I to 10 consecutive nucleotides excluding an overhang nucleotide from a 3' terminus of a sense strand of the siRNA are converted into DNA.

16. The method according to claim 10, wherein 1 to 10 consecutive nucleotides from a 5' terminus of an antisense strand of the siRNA are converted into DNA.

17. The method according to claim 10, wherein 1 to 10 consecutive nucleotides excluding an overhang nucleotide from a 3' terminus of a sense strand of the siRNA are converted into DNA and 1 to 10 consecutive nucleotides from a 5' terminus of an antisense strand of the siRNA are converted into DNA.

18. The method according to claim 10, wherein a 5' terminus of an antisense strand is monophosphorylated.

19. The method according to claim 10, wherein a 5' terminus of an antisense strand is monothiophosphorylated.

20. The method according to claim 1, wherein all or a part of a 3' overhang of a sense strand is converted to DNA.

21. The method according to claim 20, wherein 1 to 10 consecutive nucleotides excluding an overhang nucleotide from a 3' terminus of a sense strand of the siRNA are converted into DNA and 1 to 10 consecutive nucleotides from a 5' terminus of an antisense strand of the siRNA are converted into DNA.

22. The method according to claim 10, wherein all or a part of a 3' overhang of a sense strand is converted to DNA.

23. The method according to claim 22, wherein 1 to 10 consecutive nucleotides excluding an overhang nucleotide from a 3' terminus of a sense strand of the siRNA are converted into DNA and 1 to 10 consecutive nucleotides from a 5' terminus of an antisense strand of the siRNA are converted into DNA.

* * * * *

SEQUENCE LISTING

<160> NUMBER OF SEQ ID NOS: 70

<210> SEQ ID NO 1
<211> LENGTH: 2346
<212> TYPE: RNA
<213> ORGANISM: Homo sapiens

<400> SEQUENCE: 1
ccuucgcgcc cugggccauc ucccucccac cucccuccgc ggagcagcca gacagcgagg    60

```
gccccggccg ggggcagggg ggacgccccg uccggggcac ccccccggcu cugagccgcc    120
cgcggggccg gccucggccc ggagcggagg aaggagucgc cgaggagcag ccugaggccc    180
cagagucuga gacgagccgc cgccgccccc gccacugcgg ggaggagggg gaggaggagc    240
gggaggaggg acgagcuggu cgggagaaga ggaaaaaaac uuuugagacu uuuccguugc    300
cgcugggagc cggaggcgcg gggaccucuu ggcgcgacgc ugcccgcgga ggaggcagga    360
cuuggggacc ccagaccgcc ucccuuugcc gccggggacg cuugcucccu cccugccccc    420
uacacggcgu cccucaggcg ccccccauucc ggaccagccc ucgggagucg ccgacccggc    480
cucccgcaaa gacuuuuccc cagaccucgg gcgcaccccc ugcacgccgc cuucauccc    540 ggccugucuc cugagccccc gcgcauccua gacccuuucu ccuccaggag acggaucucu    600
cuccgaccug ccacagaucc ccuauucaag accacccacc uucugguacc agaucgcgcc    660
caucuagguu auuccgugg gauacugaga caccccggu ccaagccucc ccuccaccac    720
ugcgcccuuc ucccugagga ccucagcuuu cccucgaggc ccuccuaccu uuugccggga    780 gaccccagc cccugcaggg gcggggccuc cccaccacac cagcccuguu cgcgcucucg    840
gcagugccgg ggggcgccgc cucccccaug ccgccuccg ggcugcggcu gcugccgcug    900
cugcuaccgc ugcuguggcu acuggugcug acgccuggcc ggccggccgc gggacuaucc    960
accugcaaga cuaucgacau ggagcuggug aagcggaagc gcaucgaggc caucccgcggc   1020 cagauccugu ccaagcugcg gcucgccagc ccccgagcc aggggagggu gccgcccggc    1080
ccgcugcccg aggccgugcu cgcccuguac aacagcaccc gcgaccgggu ggccggggag    1140
agugcagaac cggagcccga gccugaggcc gacuacuacg ccaaggaggu cacccgcgug    1200
cuaauggugg aaacccacaa cgaaaucuau gacaaguuca agcagaguac acacagcaua    1260
uauauguucu ucaacacauc agagcccga gaagcgguac cugaacccgu guugcucucc    1320
cgggcagagc ugcgucugcu gaggcucaag uuaaaagugg agcagcacgu ggagcuguac    1380
cagaaauaca gcaacaauuc cuggcgauac cucagcaacc ggcugcuggc acccagcgac    1440
ucgccagagu gguuaucuuu ugaugucacc ggaguugugc ggcagugguu gagccggugα    1500 ggggaaauug agggcuuucg ccuuagcgcc cacugcuccu gugacagcag ggauaacaca    1560
cugcaagugg acaucaacgg guucacuacc ggccgccgag gugaccuggc caccauucau    1620
ggcaugaacc ggccuuuccu gcuucucaug gccacccgc uggagagggc ccagcaucug    1680
caaagcuccc ggcaccgccg agcccuggac accaacuauu gcuucagcuc cacggagaag    1740
aacugcugcg ugcggcagcu guacauugac uuccgcaagg accucggcug gaaguggauc    1800
cacgagccca agggcuacca ugccaacuuc ugccucgggc ccugcccuca cauuuggagc    1860 cuggacacg aguacagcaa ggccuggccc cuguacaacc agcauaaccc gggcgccucg    1920
gcggcgccgu gcugcgugcc gcaggcgcug agccgcugcc caucguguaa cuacgugggc    1980
cgcaagccca aggugggca gcuguccaac augaucgugc gcuccugcaa gugcagcuga    2040
ggucccgccc cgccccgccc cgcccggca ggccggccc caccccgccc cgcccccgcu    2100
gccuugccca ugggggcugu auuuaaggac acccgugccc caagcccacc uggggcccca    2160
uuaaagaugg agagaggacu gcggaucucu gugucauugg gcgccugccu ggggucucca    2220 uccugacgu uccccacuc ccacuccccu ucugccuccu ccugccuguc    2280
ugcacuauuc cuuugcccgg caucaaggca caggggacca gugggggaaca cuacuguagu    2340 uagauc                                                              2346
```

```
<210> SEQ ID NO 2
<211> LENGTH: 21
<212> TYPE: RNA
<213> ORGANISM: Artificial
<220> FEATURE:
<223> OTHER INFORMATION: an artificially synthesized sense strand of
      siRNA

<400> SEQUENCE: 2
ccgagaagcg guaccugaac c                                           21

<210> SEQ ID NO 3
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 3
uucagguacc gcuucucgga g                                           21

<210> SEQ ID NO 4
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 4
ccugaacccg uguugcucuc c                                           21

<210> SEQ ID NO 5
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 5
agagcaacac ggguucaggu a                                           21

<210> SEQ ID NO 6
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 6
ccuggcgaua cccucagcaac c                                          21

<210> SEQ ID NO 7
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 7
uugcugaggu aucgccagga a                                           21
```

```
<210> SEQ ID NO 8
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 8
gcgacucgcc agagugguua u                                            21

<210> SEQ ID NO 9
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 9
aaccacucug gcgagucgcu g                                            21

<210> SEQ ID NO 10
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 10
cgacucgcca gagugguuau c                                            21

<210> SEQ ID NO 11
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 11
uaaccacucu ggcgagucgc u                                            21

<210> SEQ ID NO 12
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 12
gacucgccag agugguuauc u                                            21

<210> SEQ ID NO 13
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 13
auaaccacuc uggcgagucg c                                            21

<210> SEQ ID NO 14
```

```
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 14
cucgccagag ugguuaucuu u                                              21

<210> SEQ ID NO 15
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 15
agauaaccac ucuggcgagu c                                              21

<210> SEQ ID NO 16
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 16
cgccagagug guuaucuuuu g                                              21

<210> SEQ ID NO 17
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 17
aaagauaacc acucuggcga g                                              21

<210> SEQ ID NO 18
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 18
gccagagugg uuaucuuug a                                               21

<210> SEQ ID NO 19
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 19
aaaagauaac cacucuggcg a                                              21

<210> SEQ ID NO 20
<211> LENGTH: 21
```

```
<212> TYPE: RNA
<213> ORGANISM: Artificial sequence
<220> FEATURE:
<223> OTHER INFORMATION: an artificially synthesized sense strand of
      siRNA

<400> SEQUENCE: 20
cagagugguu aucuuugau g                                            21

<210> SEQ ID NO 21
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 21
ucaaaagaua accacucugg c                                           21

<210> SEQ ID NO 22
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 22
gggauaacac acugcaagug g                                           21

<210> SEQ ID NO 23
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 23
acuugcagug uguuaucccu g                                           21

<210> SEQ ID NO 24
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 24
cacugcaagu ggacaucaac g                                           21

<210> SEQ ID NO 25
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 25
uugaugucca cuugcagugu g                                           21

<210> SEQ ID NO 26
<211> LENGTH: 21
<212> TYPE: RNA
```

```
<213> ORGANISM: Artificial sequence
<220> FEATURE:
<223> OTHER INFORMATION: an artificially synthesized sense strand of
      siRNA

<400> SEQUENCE: 26
ccaccauuca uggcaugaac c                                              21

<210> SEQ ID NO 27
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 27
uucaugccau gaaugguggc c                                              21

<210> SEQ ID NO 28
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 28
gcccuggaca ccaacuauug c                                              21

<210> SEQ ID NO 29
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 29
aauaguuggu guccagggcu c                                              21

<210> SEQ ID NO 30
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 30
gacaccaacu auugcuucag c                                              21

<210> SEQ ID NO 31
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 31
ugaagcaaua guuggugucc a                                              21

<210> SEQ ID NO 32
<211> LENGTH: 21
<212> TYPE: RNA
<213> ORGANISM: Artificial sequence
```

```
<220> FEATURE:
<223> OTHER INFORMATION: an artificially synthesized sense strand of
      siRNA

<400> SEQUENCE: 32
gaccucggcu ggaaguggau c                                          21

<210> SEQ ID NO 33
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 33
uccacuucca gccggguccgaggucc u                                    21

<210> SEQ ID NO 34
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 34
ccaagggcua ccaugccaac u                                          21

<210> SEQ ID NO 35
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 35
uuggcauggu agcccuuggg c                                          21

<210> SEQ ID NO 36
<211> LENGTH: 21
<212> TYPE: RNA
<213> ORGANISM: Artificial sequence
<220> FEATURE:
<223> OTHER INFORMATION: an artificially synthesized sense strand of
      siRNA

<400> SEQUENCE: 36
cccuguacaa ccagcauaac c                                          21

<210> SEQ ID NO 37
<211> LENGTH: 21
<212> TYPE: RNA
<213> ORGANISM: Artificial sequence
<220> FEATURE:
<223> OTHER INFORMATION: an artificially synthesized anti-sense strand
      of siRNA

<400> SEQUENCE: 37
uuaugcuggu uguacagggc c                                          21

<210> SEQ ID NO 38
<211> LENGTH: 21
<212> TYPE: DNA
<213> ORGANISM: Artificial
<220> FEATURE:
```

```
<223> OTHER INFORMATION: an artificially synthesized sense strand of
      siRNA
<220> FEATURE:
<221> NAME/KEY: misc_feature
<222> LOCATION: (1)..(13)
<223> OTHER INFORMATION: RNA

<400> SEQUENCE: 38
cacugcaagu ggacatcaac g                                             21

<210> SEQ ID NO 39
<211> LENGTH: 21
<212> TYPE: DNA
<213> ORGANISM: Artificial sequence
<220> FEATURE:
<223> OTHER INFORMATION: an artificially synthesized anti-sense strand
      of siRNA
<220> FEATURE:
<221> NAME/KEY: misc_feature
<222> LOCATION: (7)..(21)
<223> OTHER INFORMATION: RNA

<400> SEQUENCE: 39
ttgatgucca cuugcagugu g                                             21

<210> SEQ ID NO 40
<211> LENGTH: 21
<212> TYPE: DNA
<213> ORGANISM: Artificial sequence
<220> FEATURE:
<223> OTHER INFORMATION: an artificially synthesized sense strand of
      siRNA
<220> FEATURE:
<221> NAME/KEY: misc_feature
<222> LOCATION: (1)..(14)
<223> OTHER INFORMATION: RNA

<400> SEQUENCE: 40
cacugcaagu ggacatcaac g                                             21

<210> SEQ ID NO 41
<211> LENGTH: 21
<212> TYPE: DNA
<213> ORGANISM: Artificial sequence
<220> FEATURE:
<223> OTHER INFORMATION: an artificially synthesized anti-sense strand
      of siRNA
<220> FEATURE:
<221> NAME/KEY: misc_feature
<222> LOCATION: (6)..(21)
<223> OTHER INFORMATION: RNA

<400> SEQUENCE: 41
ttgatgucca cuugcagugu g                                             21

<210> SEQ ID NO 42
<211> LENGTH: 21
<212> TYPE: DNA
<213> ORGANISM: Artificial sequence
<220> FEATURE:
<223> OTHER INFORMATION: an artificially synthesized sense strand of
      siRNA
<220> FEATURE:
<221> NAME/KEY: misc_feature
<222> LOCATION: (1)..(15)
<223> OTHER INFORMATION: RNA

<400> SEQUENCE: 42
cacugcaagu ggacatcaac g                                             21
```

<210> SEQ ID NO 43
<211> LENGTH: 21
<212> TYPE: DNA
<213> ORGANISM: Artificial sequence
<220> FEATURE:
<223> OTHER INFORMATION: an artificially synthesized anti-sense strand
    of siRNA
<220> FEATURE:
<221> NAME/KEY: misc_feature
<222> LOCATION: (5)..(21)
<223> OTHER INFORMATION: RNA

<400> SEQUENCE: 43
ttgaugucca cuugcagugu g                                              21

<210> SEQ ID NO 44
<211> LENGTH: 21
<212> TYPE: DNA
<213> ORGANISM: Artificial sequence
<220> FEATURE:
<223> OTHER INFORMATION: an artificially synthesized sense strand of
    siRNA
<220> FEATURE:
<221> NAME/KEY: misc_feature
<222> LOCATION: (1)..(16)
<223> OTHER INFORMATION: RNA

<400> SEQUENCE: 44
cacugcaagu ggacaucaac g                                              21

<210> SEQ ID NO 45
<211> LENGTH: 21
<212> TYPE: DNA
<213> ORGANISM: Artificial sequence
<220> FEATURE:
<223> OTHER INFORMATION: an artificially synthesized anti-sense strand
    of siRNA
<220> FEATURE:
<221> NAME/KEY: misc_feature
<222> LOCATION: (4)..(21)
<223> OTHER INFORMATION: RNA

<400> SEQUENCE: 45
ttgaugucca cuugcagugu g                                              21

<210> SEQ ID NO 46
<211> LENGTH: 21
<212> TYPE: DNA
<213> ORGANISM: Artificial sequence
<220> FEATURE:
<223> OTHER INFORMATION: an artificially synthesized sense strand of
    siRNA
<220> FEATURE:
<221> NAME/KEY: misc_feature
<222> LOCATION: (1)..(17)
<223> OTHER INFORMATION: RNA

<400> SEQUENCE: 46
cacugcaagu ggacaucaac g                                              21

<210> SEQ ID NO 47
<211> LENGTH: 21
<212> TYPE: DNA
<213> ORGANISM: Artificial sequence
<220> FEATURE:
<223> OTHER INFORMATION: an artificially synthesized anti-sense strand
    of siRNA
<220> FEATURE:
<221> NAME/KEY: misc_feature
<222> LOCATION: (3)..(21)

```
<223> OTHER INFORMATION: RNA

<400> SEQUENCE: 47
ttgaugucca cuugcagugu g                                              21

<210> SEQ ID NO 48
<211> LENGTH: 21
<212> TYPE: DNA
<213> ORGANISM: Artificial sequence
<220> FEATURE:
<223> OTHER INFORMATION: an artificially synthesized sense strand of
      siRNA
<220> FEATURE:
<221> NAME/KEY: misc_feature
<222> LOCATION: (1)..(18)
<223> OTHER INFORMATION: RNA

<400> SEQUENCE: 48
cacugcaagu ggacaucaac g                                              21

<210> SEQ ID NO 49
<211> LENGTH: 21
<212> TYPE: DNA
<213> ORGANISM: Artificial sequence
<220> FEATURE:
<223> OTHER INFORMATION: an artificially synthesized anti-sense strand
      of siRNA
<220> FEATURE:
<221> NAME/KEY: misc_feature
<222> LOCATION: (2)..(21)
<223> OTHER INFORMATION: RNA

<400> SEQUENCE: 49
tugaugucca cuugcagugu g                                              21

<210> SEQ ID NO 50
<211> LENGTH: 21
<212> TYPE: DNA
<213> ORGANISM: Artificial sequence
<220> FEATURE:
<223> OTHER INFORMATION: an artificially synthesized sense strand of
      siRNA
<220> FEATURE:
<221> NAME/KEY: misc_feature
<222> LOCATION: (1)..(19)
<223> OTHER INFORMATION: RNA

<400> SEQUENCE: 50
cacugcaagu ggacaucaac g                                              21

<210> SEQ ID NO 51
<211> LENGTH: 21
<212> TYPE: DNA
<213> ORGANISM: Artificial sequence
<220> FEATURE:
<223> OTHER INFORMATION: an artificially synthesized sense strand of
      siRNA
<220> FEATURE:
<221> NAME/KEY: misc_feature
<222> LOCATION: (1)..(20)
<223> OTHER INFORMATION: RNA

<400> SEQUENCE: 51
cacugcaagu ggacaucaac g                                              21

<210> SEQ ID NO 52
<211> LENGTH: 21
<212> TYPE: DNA
<213> ORGANISM: Artificial sequence
```

```
<220> FEATURE:
<223> OTHER INFORMATION: an artificially synthesized sense strand of
      siRNA
<220> FEATURE:
<221> NAME/KEY: misc_feature
<222> LOCATION: (1)..(13)
<223> OTHER INFORMATION: RNA

<400> SEQUENCE: 52
ccaagggcua ccatgccaac t                                                    21

<210> SEQ ID NO 53
<211> LENGTH: 21
<212> TYPE: DNA
<213> ORGANISM: Artificial sequence
<220> FEATURE:
<223> OTHER INFORMATION: an artificially synthesized anti-sense strand
      of siRNA
<220> FEATURE:
<221> NAME/KEY: misc_feature
<222> LOCATION: (7)..(21)
<223> OTHER INFORMATION: RNA

<400> SEQUENCE: 53
ttggcauggu agcccuuggg c                                                    21

<210> SEQ ID NO 54
<211> LENGTH: 23
<212> TYPE: RNA
<213> ORGANISM: Artificial
<220> FEATURE:
<223> OTHER INFORMATION: an artificially synthesized sense strand of
      siRNA

<400> SEQUENCE: 54
cacacugcaa guggacauca acg                                                  23

<210> SEQ ID NO 55
<211> LENGTH: 23
<212> TYPE: RNA
<213> ORGANISM: Artificial
<220> FEATURE:
<223> OTHER INFORMATION: an artificially synthesized anti-sense strand
      of siRNA

<400> SEQUENCE: 55
cguugauguc cacuugcagu gug                                                  23

<210> SEQ ID NO 56
<211> LENGTH: 21
<212> TYPE: DNA
<213> ORGANISM: Artificial
<220> FEATURE:
<223> OTHER INFORMATION: an artificially synthesized anti-sense strand
      of siRNA
<220> FEATURE:
<221> NAME/KEY: misc_feature
<222> LOCATION: (1)..(19)
<223> OTHER INFORMATION: RNA

<400> SEQUENCE: 56
uugaugucca cuugcagugt g                                                    21

<210> SEQ ID NO 57
<211> LENGTH: 21
<212> TYPE: DNA
<213> ORGANISM: Artificial
<220> FEATURE:
<223> OTHER INFORMATION: an artificially synthesized sense strand of
```

```
                              siRNA
<220> FEATURE:
<221> NAME/KEY: misc_feature
<222> LOCATION: (1)..(18)
<223> OTHER INFORMATION: RNA

<400> SEQUENCE: 57
cacugcaagu ggacaucakc g                                              21

<210> SEQ ID NO 58
<211> LENGTH: 22
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 58
cacugcaagu ggacaucaac gt                                             22

<210> SEQ ID NO 59
<211> LENGTH: 23
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 59
cacugcaagu ggacaucaac gtt                                            23

<210> SEQ ID NO 60
<211> LENGTH: 24
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 60
cacugcaagu ggacaucaac gttt                                           24

<210> SEQ ID NO 61
<211> LENGTH: 25
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 61
cacugcaagu ggacaucaac gtttt                                          25
```

```
<210> SEQ ID NO 62
<211> LENGTH: 26
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 62
cacugcaagu ggacaucaac gttttt                                            26

<210> SEQ ID NO 63
<211> LENGTH: 27
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 63
cacugcaagu ggacaucaac gtttttt                                           27

<210> SEQ ID NO 64
<211> LENGTH: 28
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 64
cacugcaagu ggacaucaac gttttttt                                          28

<210> SEQ ID NO 65
<211> LENGTH: 23
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 65
cacugcaagu ggacaucaac gta                                               23

<210> SEQ ID NO 66
<211> LENGTH: 25
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA
```

```
<400> SEQUENCE: 66
cacugcaagu ggacaucaac gttaa                                              25

<210> SEQ ID NO 67
<211> LENGTH: 27
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 67
cacugcaagu ggacaucaac gtttaaa                                            27

<210> SEQ ID NO 68
<211> LENGTH: 29
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 68
cacugcaagu ggacaucaac gttttaaaa                                          29

<210> SEQ ID NO 69
<211> LENGTH: 25
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 69
cacugcaagu ggacatcaac gttaa                                              25

<210> SEQ ID NO 70
<211> LENGTH: 27
<212> TYPE: DNA
<213> ORGANISM: Artificial
<220> FEATURE:
<223> OTHER INFORMATION: an artificially synthesized sense strand of
      siRNA
<220> FEATURE:
<221> NAME/KEY: misc_feature
<222> LOCATION: (1)..(21)
<223> OTHER INFORMATION: RNA

<400> SEQUENCE: 70
cacugcaagu ggacatcaac gtttaaa                                            27
```